US011149282B2

(12) United States Patent
Chappell et al.

(10) Patent No.: US 11,149,282 B2
(45) Date of Patent: Oct. 19, 2021

(54) SYSTEMS AND METHODS FOR THE PRODUCTION OF LINEAR AND BRANCHED-CHAIN HYDROCARBONS

(71) Applicant: University of Kentucky Research Foundation, Lexington, KY (US)

(72) Inventors: Joe Chappell, Lexington, KY (US); Shuiqin Wu, San Diego, CA (US)

(73) Assignee: UNIVERSITY OF KENTUCKY RESEARCH FOUNDATION, Lexington, KY (US)

( * ) Notice: Subject to any disclaimer, the term of this patent is extended or adjusted under 35 U.S.C. 154(b) by 0 days.

(21) Appl. No.: 13/573,709

(22) Filed: Oct. 3, 2012

(65) Prior Publication Data

US 2013/0198896 A1    Aug. 1, 2013

Related U.S. Application Data

(60) Provisional application No. 61/542,689, filed on Oct. 3, 2011.

(51) Int. Cl.
*C12N 15/82* (2006.01)
*C12N 9/10* (2006.01)
*C12N 9/90* (2006.01)

(52) U.S. Cl.
CPC ....... *C12N 15/8243* (2013.01); *C12N 9/1085* (2013.01); *C12N 9/90* (2013.01); *C12Y 205/0101* (2013.01)

(58) Field of Classification Search
None
See application file for complete search history.

(56) References Cited

U.S. PATENT DOCUMENTS

2003/0236208 A1* 12/2003 Kmiec et al. ............... 514/44
2009/0178160 A1*  7/2009 Park et al. ................. 800/287
2010/0041120 A1*  2/2010 Chappell et al. ........... 435/166

OTHER PUBLICATIONS

Wu et al., 2006, Nature Biotechnology 24: 1441-1447, with supplementary information.*
Mercke et al., 2000, Archives of Biochemistry and Biophysics 381: 173-180.*
Korn, 2010, New Phytologist 187: 9-13.*
Kim et al., 2011, Plant Cell Physiology 52: 125-137.*
Robinson et al., 1993, Molecular and Cellular Biology 13: 2706-2717.*
Golz et al., 2002, Current Biology 12: 515-522.*
Gavin et al., 2006, Nature 440: 631-636.*
Aldridge et al., 2009, FEBS Journal 276: 1177-1186.*
Li and Chiu, 2010, Annual Review of Plant Biology 61: 157-180.*
Meadows et al., 1989, FEBS Letters 253: 244-246.*
Benfey PN, Chua NH; The Cauliflower Mosaic Virus-35s Promoter—Combinatorial Regulation of Transcription in Plants. (1990) Science 250: 959-966.
Ennajdaoui H, Vachon G, Giacalone C, Besse I, Sallaud C, Herzog M, Tissier A (2010) Trichome specific expression of the tobacco (*Nicotiana sylvestris*) cembratrien-ol synthase genes is controlled by both activating and repressing cis-regions. Plant Molecular Biology 73: 673-685.
Hillen LW, Pollard G, Wake LV, White N (1982) Hydrocracking of the Oils of Botryococcus-Braunii to Transport Fuels. Biotechnology and Bioengineering 24: 193-205.
Niehaus, Tom, Identification of unique mechanisms for triterpene biosynthesis in Botryococcus braunii, PNAS, 12260-12265.
Verdaguer B, deKochko A, Beachy RN, Fauquet C (1996) Isolation and expression in transgenic tobacco and rice plants, of the cassava vein mosaic virus (CVMV) promoter. Plant Molecular Biology 31: 1129-1139.
Wagner GJ, Wang E, Shepherd RW (2004) New approaches for studying and exploiting an old protuberance, the plant trichome. Annals of Botany 93: 3-11.
Wang EM, Gan SS, Wagner GJ (2002) Isolation and characterization of the CYP71D16 trichome-specific promoter from Nicotiana tabacum L. Journal of Experimental Botany 53: 1891-1897.
Wu SQ, Schalk M, Clark A, Miles RB, Coates R, Chappell J Redirection of cytosolic or plastidic isoprenoid precursors elevates terpene production in plants. (2006) Nature Biotechnology 24: 1441-1447.
Robinson, et al. Conservation between Human and Fungal Squalene Synthetases: Similarities in Structure, Function, and Regulation, Molecular and Cellular Biology, vol. 13, No. 5 May 1993, p. 2706-2717.
Bell, et al. Structure-Function Mapping of Key Determinants for Hydrocarbon Biosynthesis by Squalene and Squalene Synthase-like Enzymes from the Green Alga *Botryococcus braunii* Race B, Biochemistry 2014, 53, 7570-7581.
Kempinski, et al.; Metabolic Engineering of Higher Plants and Algae for Isoprenoid Production; Adv Biochem Eng Biotechnol (2015) 148: 161-199.

* cited by examiner

*Primary Examiner* — Bratislav Stankovic
(74) *Attorney, Agent, or Firm* — Stites & Harbison, PLLC; Stephen J. Weyer, Esq.

(57) ABSTRACT

A system and method is provided for producing linear and branched hydrocarbons and in particular triterpenes in plant cells. The system and method includes a transformed plant cell with an isolated nucleic acid encoding a farnesyl diphosphate synthase (FPS) and with an isolated nucleic acid encoding a triterpene synthase.

39 Claims, 5 Drawing Sheets

Specification includes a Sequence Listing.

| construct | Plant line | Leaf development | Squalene (µg/gm fr.wt.) |
|---|---|---|---|
| Wild type | wt | intermediate | 0.4 |
| Constitutive, cytosolic (MVA) targeted | # 16 | young | 6.4 |
| | | intermediate | 5.5 |
| | | mature | 7.4 |
| Constitutive, plastidic (MEP) targeted | # 7 | young | 30.1 |
| | | intermediate | 121.2 |
| | | mature | 147.4 |
| | # 15 | young | 329.3 |
| | | intermediate | 450.4 |
| | | mature | 667.5 |
| Trichome, plastidic (MEP) targeted | # 31 | young | 527.6 |
| | | intermediate | 594.7 |
| | | mature | 1,760.2 |

Figure 4

SYSTEMS AND METHODS FOR THE PRODUCTION OF LINEAR AND BRANCHED-CHAIN HYDROCARBONS

CROSS-REFERENCE TO RELATED APPLICATION

This application claims the benefit of U.S. Provisional Patent application Ser. No. 61/542,689 filed Oct. 3, 2011, herein incorporated by reference.

FIELD OF THE INVENTION

The presently-disclosed subject matter relates to systems and methods for the production of linear and branched-chain hydrocarbons, such as triterpenes. In particular, the presently-disclosed subject matter relates to transgenic plants for use in the production of triterpenes as an alternative source for biofuels and petrochemicals.

BACKGROUND OF THE INVENTION

Oil shale deposits consist of high concentrations of linear, branched-chain hydrocarbons, which when processed via standard oil refinement processes yield chemicals constituents that are utilized by diverse industrial sectors for the production of polymers (i.e. nylon and PVC), oils, paints, and fine chemicals for personal (i.e. cosmetics) and a variety of industrial applications (i.e. detergents and processed food manufacturing), as well as for combustible fuels (gasoline, diesel and jet fuels). Triterpenes are linear, branched-chain hydrocarbons and are considered to be major progenitors to the existing oil shale deposits.

Linear, branched-chain triterpenes (compounds containing a 30 carbon (C30) atom scaffold) are chemicals having direct commercial value to the personal health care (i.e. oil base for cosmetics, topical skin care products) and food manufacturing (i.e. emulsifiers) industries, and when subjected to standard hydrocracking processes yield chemical intermediates of value for chemical manufacturing (i.e. nylons, oils and plastics). Of equal or greater value, hydrocracked triterpenes are readily distilled to combustible fuels (gasoline, jet fuel and diesel) in yields approaching 97% [Hillen, 1982].

Triterpenes are found ubiquitously in nature, in bacteria, fungi, plants and man. However, triterpenes only accumulate in select organisms. For instance, squalene accounts from 16 to 80% of the oil extracted from in shark liver. Shark liver was the most common source of squalene for many of its applications until the late 1990's when harvesting of sharks for their livers was recognized as an unsustainable and ecologically unsound practice, and strongly discouraged worldwide.

Several plant materials but especially olive oil are considered alternative sources for squalene. However, the squalene content of olive oil is only 0.1 to 0.7%, which requires extensive and costly purification methodologies to properly prepare, and is obtained from a crop that is costly to produce and limited in production capacity. Hence, the present inventors have developed and disclose herein systems, methods, and plants engineered for high-level production of triterpenes in a scalable, renewable and sustainable production platform.

BRIEF DESCRIPTION OF THE DRAWINGS

FIG. 4 shows evidence for diverting carbon flux from the mevalonate (MVA, cytosolic) or the methyl-erythritol phosphate (MEP, plastidic) pathways for novel squalene biosynthesis and accumulation. Gene constructs used to engineer squalene metabolism in the cytoplasm consisted of a truncated form of the yeast squalene synthase (ySQS) gene (SEQ ID NO: 4) and the avian farnesyl diphosphate synthase (FPS) gene (SEQ ID NO: 5) inserted downstream of strong, constitutive promoters (Pca, 35S cauliflower mosaic viral promoter; Pcv, cassava vein mosaic viral promoter) or enhanced, trichome specific promoters (e, 35S enhancer; cbts, cyp16, cembriene synthase and hydroxylase promoters, respectively), and were identical for plastid engineering except a plastid targeting signal sequence (tp) (SEQ ID NO: 6) was fused to the 5' end of the respective genes. Wild type tobacco (Nicotiana tabacum accession 1068) was transformed with the respective gene constructs and antibiotic selected $R_0$ lines propagated in the greenhouse were assessed from squalene accumulation by GC-MS.

SUMMARY OF THE INVENTION

Figure 1:
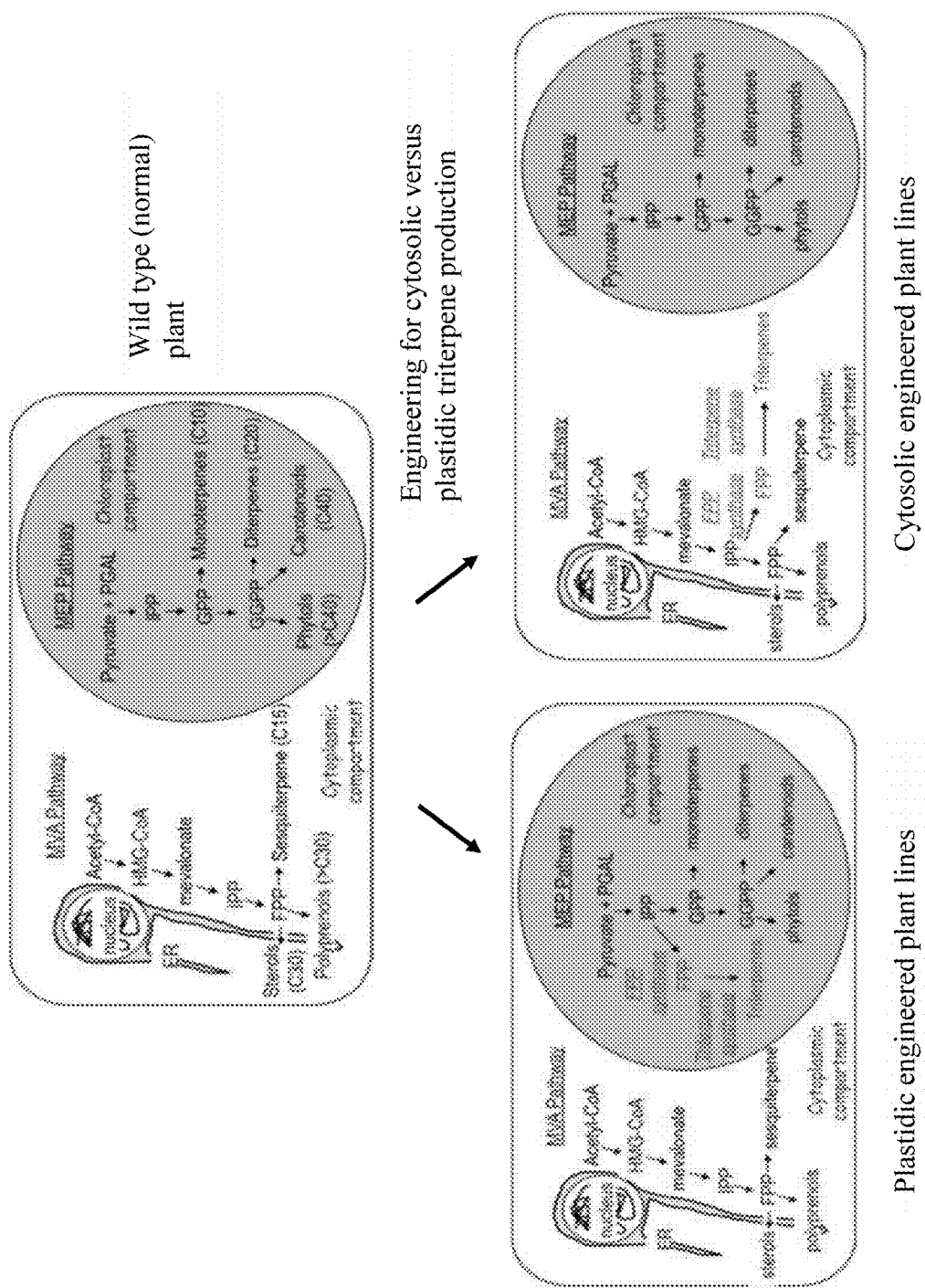
FIG. 1 is a diagram of a strategy for engineering triterpene metabolism into two different cellular compartments of plants—the cytoplasm and chloroplast compartments, in accordance with the present invention.

As disclosed herein, the present inventors have developed the means for producing linear, branched-chain hydrocarbons in high yield in transgenic plants as a potential replacement source for biofuels and petrochemicals used in diverse industrial manufacturing processes.

The present invention is directed to a unique system and method for producing linear and branch-chain hydrocarbons in plant cells. In particular, the system and method includes transforming plant cells with an isolated nucleic acid encoding a farnesyl diphosphate synthase (FPS) and with an isolated nucleic acid encoding a triterpene synthase. In one form, the FPS is an avain FPS such as one encoded by SEQ ID NO: 5, disclosed herein. Alternatively, the FPS may be encoded by or have the amino acid sequence of SEQ ID NOS: 7-16, disclosed herein. In various alternative forms of the system and method the triterpene synthases can be encoded by or have the amino acid sequence of SEQ ID NOS: 17-27, herein disclosed.

In various alternative forms, the system and method include directing FPS and the triterpene synthase specifically to the chloroplast. This may be achieved by using an isolated nucleic acid such as an expression vector which encodes an amino acid sequence added to the N-terminus end of the FPS and the triterpene synthase amino acid sequence thereby directing the respective enzymes to the chloroplast. An exemplar sequence is provided by SEQ ID NO: 1, disclosed herein.

The present invention in one form is directed to a method for producing triterpene in a plant which comprises transforming a plant cell within an isolated nucleic acid encoding a FPS and an isolated nucleic acid encoding a triterpene synthase.

The present invention in another form thereof relates to a transgenic plant cell which comprises an isolated nucleic acid encoding a FPS and an isolated nucleic acid encoding a triterpene synthase wherein co-expression of the FPS and triterpene synthase increases an amount of triterpenes in the plant cell over a wild-type plant cell.

The present invention, in another form thereof relates to a method for increasing triterpene production in a plant comprising transforming a plant cell with a first isolated nucleic acid encoding a FPS and a second isolated nucleic acid encoding a triterpene synthase, wherein co-expression of the FPS and triterpene synthase increases an amount of triterpene in the plant.

DETAILED DESCRIPTION

The present system and method will now be described with regard to specific embodiments and experiments. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by one of ordinary skill in the art, definitions are set forth herein to facilitate explanation of the presently-disclosed subject matter. Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The presently-disclosed subject matter includes systems and methods for production of triterpenes in plants. In particular, the present system and method are directed to increasing plant cell production of linear and branched-chain hydrocarbons, namely triterpenetriterpenes. The system and method includes transforming a plant cell using isolated nucleic acid sequences which encode specific enzymes which enhance the production of the aforementioned linear and branched triterpenetriterpenes. The enzymes include a combination of a farnesyl diphosphate synthase (FPS) such as avain FPS in combination with a triterpenetriterpene synthase. The combination of the two enzymes and in particular their overexpression in the transformed plant cell results in enhanced linear and branched triterpene production as compared with wild-type plant cells.

The present system and method in one advantageous form includes specifically targeting the FPS and the triterpene synthase to the chloroplast as a way for generating additional triterpene production within the chloroplast. This targeting of enzymes can be achieved by modifying the nucleic acid sequence encoding the FPS and triterpene synthase with an amino acid sequence such as one at the end terminus which specifically targets the enzymes to the chloroplast.

Possible FPS's include avain FPS such as one encoded by SEQ ID NO: 5. Others include farnesyl diphosphate synthase also known as farnesyl pyrophosphate synthase (FPP synthase) include FPS 2 protein from *Arabidopsis* having amino acid sequence SEQ ID NO: 7 or encoded by mRNA, SEQ ID NO: 8 and FPS 1 protein from *Arabidopsis* having amino acid sequence SEQ ID NO: 9 and one encoded by mRNA, SEQ ID NO: 10, all disclosed herein. Still others include FPP synthase from yeast (*Saccharomyces cerevisiae*) known as ERG 20 gene such as one having the amino acid sequence of SEQ ID NO: 11 or encoded by mRNA of SEQ ID NO: 12; human FPP synthase such as one having the amino acid sequence of SEQ ID NO: 13 or encoded by mRNA having SEQ ID NO: 14; FPP synthase from alga, *Chlamydomonas reinhardtii* such as one having the amino acid sequence of SEQ ID NO: 15 or encoded by mRNA having the sequence of SEQ ID NO: 16.

Possible triterpene synthases include yeast squalene synthase such as one encoded by a nucleic acid having a sequence of SEQ ID NO: 17, having a carboxy-terminal (3' terminal) truncation which removes a membrane spanning domain. Other triterpene synthases include *Botryococcus braunii* (alga) Race B squalene synthase encoded by SEQ ID NO: 18; *Arabidopsis thaliana* 3' truncated squalene synthase encoded by SEQ ID NO: 19; *Nicotiona tabacum* 3' truncated squalene synthase encoded by SEQ ID NO: 20; and Rat 3' truncated squalene synthase encoded by SEQ ID NO: 21.

Still others triterpene synthases included squalene synthase-like 2 gene from *Botryococcus* encoded by SEQ ID NO: 22 or one having the amino acid sequence of SEQ ID NO: 23; and squalene synthase-like 1 gene from *Botryococcus* encoded by SEQ ID NO: 24 or having the amino acid sequence of SEQ ID NO: 25. Still others include co-expression of SSL-1 and SSL-3, either as separate genes, or fused via a linker domain to encode a hybrid fused protein such as one encoded by SEQ ID NO: 26 or having the amino acid sequence of SEQ ID NO: 27. Additional triterpene synthesis include those described and disclosed in Niehaus (2011) "Identification of unique mechanisms for triterpene biosynthesis in *Botryococcus braunii*", herein incorporated by reference.

The methods described herein provide various alternative means for generating high levels of triterpene materials with a reliable and cost effective production platform. For example, expression of a farnesyl diphosphate synthase targeted to the plastid compartment of plant cells provides a unique means for diverting photosynthetically fixed $CO_2$ to the generation of farnesyl diphosphate, FPP, a key precursor for triterpene biosynthesis. Co-expression and plastid targeting of a triterpene synthase, like squalene synthase, to the plastid compartment further converts the accumulated FPP to squalene for direct manufacturing and industrial utility. Alternative triterpene synthases that may be substituted for squalene synthase include botryococcene synthase, and thus create alternative triterpene backbones. Still others include those encoded by or having amino acid sequences of SEQ ID NOS: 17-27 and those disclosed in Niehaus (2011).

These triterpene backbones may also be further modified by co-expressing other decorating enzymes like triterpene methyltransferases to make mono-, di-, and tetra-methylated triterpenes, compounds of enhanced utility for chemical and biofuels production. Alternatively, other triterpene synthase genes could be engineered similarly to generate other valuable cyclized compounds like β-amyrin. For example, co-expression of squalene epoxidase and β-amyrin synthase in plants over-expressing un-regulated forms of FPP synthase and squalene synthase would provide a new source of β-amyrin, a cyclized triterpene molecule of importance in the development of new pharmaceuticals.

EXAMPLES

The present system and method will now be described with regard to specific examples which provide additional understanding of the present system and method. However, additional examples are possible and will be readily apparent to one of ordinary skill in the art based on the present disclosure.

Evidence for the engineering of triterpene metabolism. The present inventors have developed strategies for engineering triterpene metabolism. The target for initial studies was squalene, and the aim was to determine if an analogous strategy as used for sesquiterpenes was applicable to squalene. The first construct iterations were designed to over-express squalene synthase (SQS) in combination with the avian farnesyl diphosphate synthase (FPS) (SEQ ID NO: 5), with the encoded enzymes targeted either to the MVA pathway (cytoplasm) or to the MEP pathway (plastid) (FIG. 1). Because squalene synthase is natively tethered to the endoplasmic reticulum via a carboxy-terminal hydrophobic domain, the present inventors first screened truncated versions of squalene synthase for soluble catalytic activity.

Figure 2:
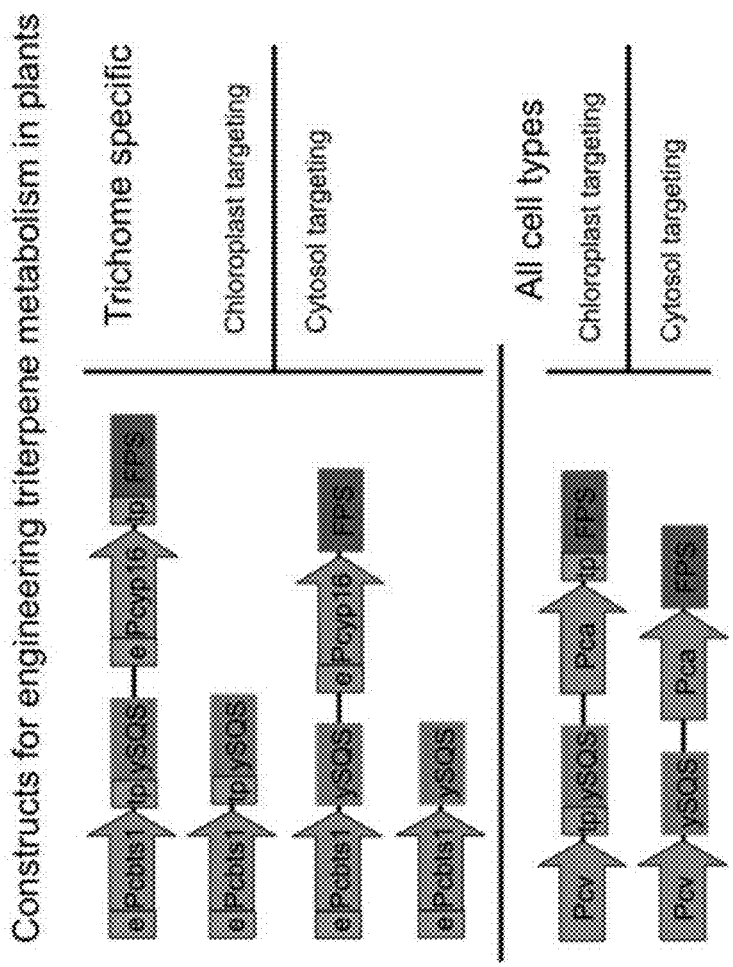
FIG. 2 is a diagram of a constructs designed and assembled to engineer triterpene metabolism in plants in accordance with the present invention in which the DNA sequences were assembled together using standard molecular biology methods and the DNA sequences for the various elements are noted below. The expression cassettes were introduced into a Ti plasmid vector, the engineered Ti plasmid vectors introduced into Agrobacterium tumefaciens, and the resulting Agrobacterium lines used to genetic engineer Nicotiana tabacum plants, all as described previously by Wu et al. [Wu, 2006].

This was accomplished by inserting 3' truncated versions of the rat, yeast (SEQ ID NO: 4), tobacco, *Arabidopsis* and *Botryococcus* squalene synthase genes into a bacterial expression vector, then evaluating the level of soluble squalene synthase activity in the bacterial lysates after gene induction treatment. The truncated yeast squalene synthase gene (ySQS) (SEQ ID NO: 4) yielded the highest level of soluble squalene synthase activity in comparison to the others and hence was chosen for a subsequent vector construction (FIG. 2).

Figure 3:
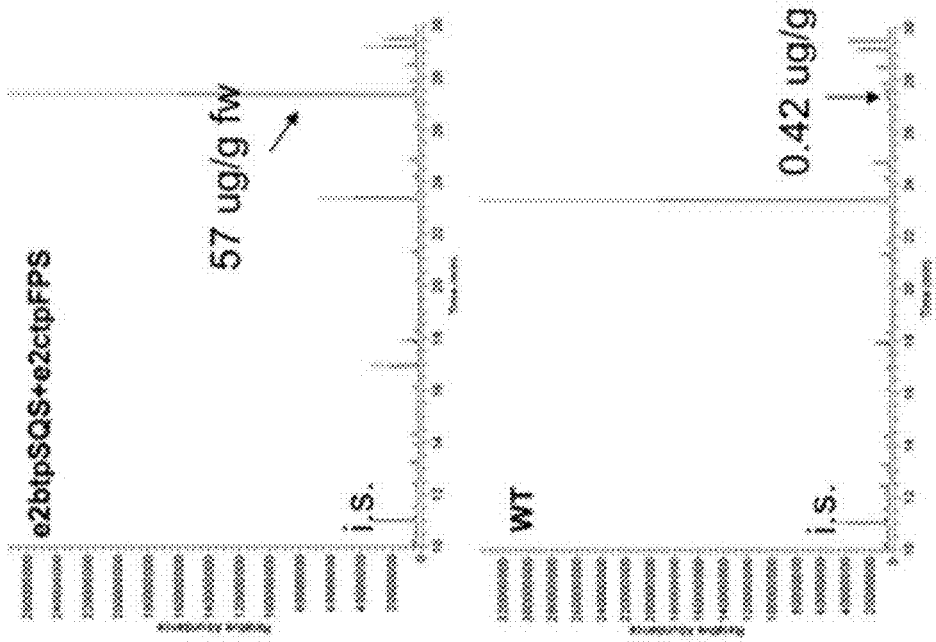
FIG. 3 comprises panels (a)-(c) depicting chemical characterization of transgenic tobacco lines. One hundred to 500 mg of transgenic material were collected for chemical analyses. Each sample was ground in liquid nitrogen and extracted with a hexane:ethyl acetate mixture (v/v 85:15) containing 200 ng of α-cedrene as an internal standard (i.s.). The extracts were partially purified by passing through a silica column (500 mg) and further eluted by 1 ml of the hexane solvent. After concentration of the eluate under a stream of nitrogen, aliquots were injected onto a GC-MS equipped with a Rtx-5 capillary column (30 m×0.32 mm, 0.25 μm phase thickness) with the following temperature program of 70° C. for 1 min, followed by a 4° C. per min gradient to 250° C. Mass spectra were recorded at 70 eV, scanning from 35 to 500 atomic mass units, and experimental samples were compared to authentic standards of squalene for verification. Twenty to forty independent transgenic lines (line #) were generated per construct and the analysis for a few selected lines are shown for illustration.

Expression of the cytosolic and plastid targeted (tp, transit peptide of the *Arabidopsis* RuBisCO small-subunit protein appended to the amino terminal end of the respective genes to direct the desired proteins to the chloroplast compartment) genes were driven by either strong constitutive promoters (cauliflower/cassava mosaic viral promoters [Wu, 2006]) or trichome specific promoters (cbts, cembratrienol synthase [Ennajdaoui, 2010] and cyt16, diterpene hydroxylase [Wang, 2002]. The tissue specific promoters were also enhanced for gene expression by adding an iterative 35S CAMV enhancer element [Benfey, 1990] onto the constructs. The respective expression cassettes were then used to generate independent tobacco transgenic lines and the initial Ro plants were screened for their ability to accumulate squalene by GC-MS analysis. Example data for this preliminary screen are presented in FIG. 3.

Squalene does not accumulate to any appreciable level in wild type plants and borders on being within the technical detection limits of GC-MS. While plants engineered with the squalene synthase and FPS enzymes targeted to the cytosolic MVA pathway appeared normal in terms of growth habit and stature, 16 of 30 lines surveyed accumulated upwards of 10-times higher levels of squalene than the wild type controls. In comparison, about 20% of the plants engineered for plastid targeting of the SS and FPS proteins exhibited some growth abnormalities, mostly stunted growth. Seven of the $R_0$ transgenic lines tested up to this point accumulated much higher levels (>100×) of squalene than the control plants or those having their cytosolic MVA pathway engineered (FIG. 4).

Interestingly, no correlation between growth characteristics and squalene accumulation was observed. For instance, plant line #15 grew comparable to control plant while plant line #7 was stunted. Nonetheless, plant #15 accumulated 1,200 times more squalene than control plants while #7 accumulated about a 300-fold greater amount. A modest, yet positive correlation between leaf developmental age and squalene accumulation was also evident for the lines engineered for squalene biosynthesis in the chloroplasts, but much less so for the cytosolic engineered lines.

By far the greatest amount of squalene accumulation was documented for plants engineered for trichome specific expression of the squalene synthase and FPS proteins targeted to the chloroplast compartment. The intent of this expression vector design was to facilitate trichome specific expression in hopes that whatever squalene might be produced, it would be secreted and/or sequestered similarly to the diterpenes and sucrose esters that normally accumulate as leaf exudates [Wagner, 2004]. The observed levels of approximately 1 mg squalene per g fresh weight of leaf tissue are upwards of several thousand-fold higher than in the wild type control plants. The accumulation pattern also exhibits a modest correlation with leaf development and some of the high and low squalene accumulating plants do exhibit various degrees of stunted growth.

If one assumes water weight accounts for about 90% of the leaf fresh weight, then the levels of squalene accumulating (0.5-1.7 mg/g fresh weight) approach 5 to 10 mg per g dry weight, which corresponds to approximately 0.5 to 1% of the plant material dry weight. Such a calculation is undoubtedly preliminary at this stage. Nonetheless, one milestone often discussed as being necessary for the commercialization of chemical targets produced in plants is accumulation to 1 to 4% of the plant dry weight.

Figure 5:
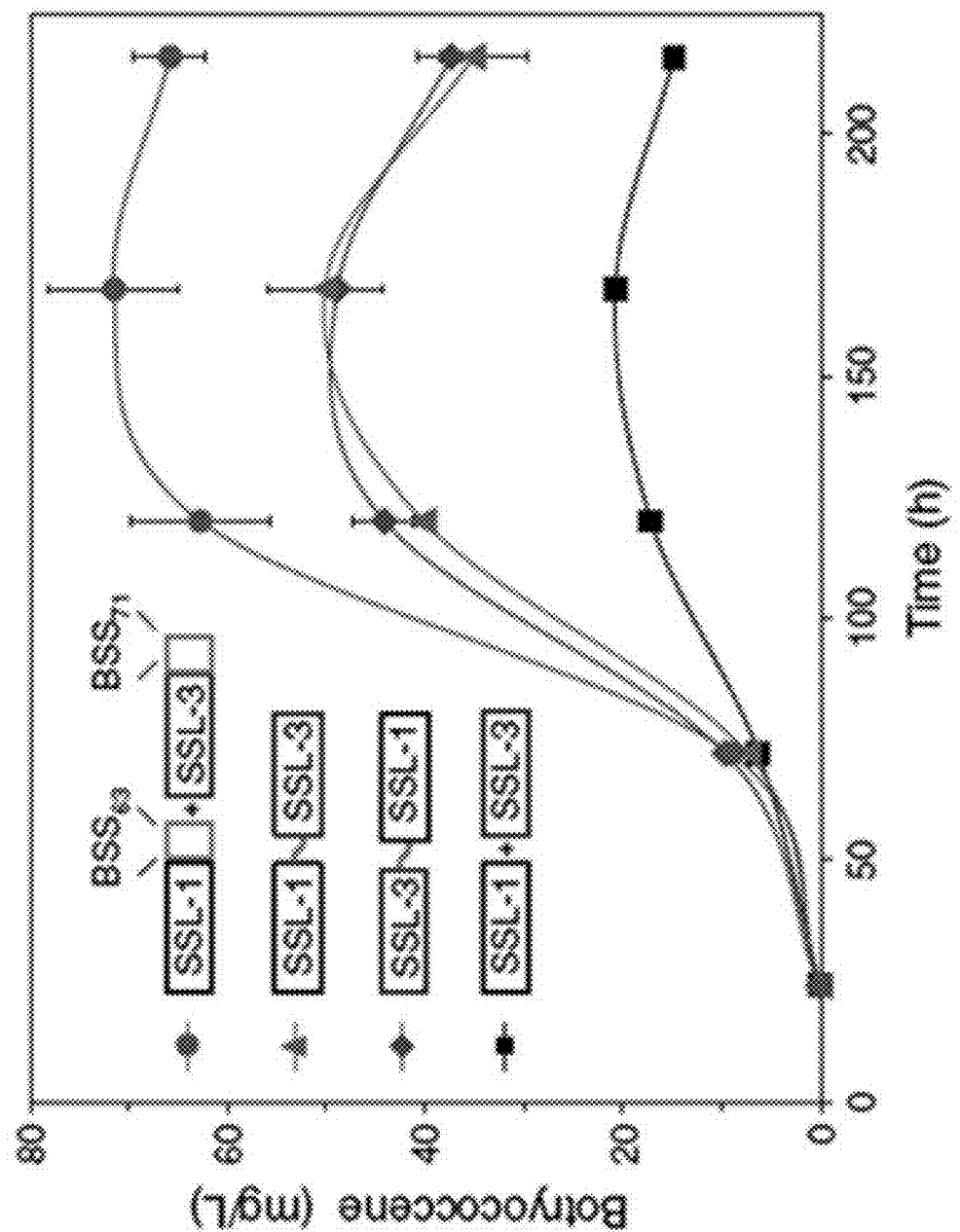
FIG. 5 is a graph illustrating how over-express SSL-1 and SSL-3 with different configurations yield botryococcene production.

In one further example, SSL-1 and SSL-3 were over expressed in various configurations to yield botryococcene. The SSL-1 and SSL-3 produced enhanced botryococcene production as shown in FIG. 5. In particular, FIG. 5 shows a comparison of botryococcene production in yeast engineered with different configurations of SSL-1 and SSL-3. Yeast line TN7 was engineered with SSL-1 and SSL-3 genes on separate plasmids (squares), with gene fusions [SSL-1 fused to SSL-3 via a triplet repeat of GGSG (triangles), or vice versa (diamonds), or with 63 or 71 amino acids of the carboxy terminus of the *Botryococcus* squalene synthase, sequences containing a membrane spanning domain, appended to the carboxy termini of the SSL-1 and SSL-3 enzymes, respectively (circles). The data represents mean±S.E.M. The over expression constructs and experiments preformed as described in Niehaus (2011).

Throughout this document, various references are mentioned. All such references are incorporated herein by reference, including the references set forth in the following list:

REFERENCES

Benfey P N, Chua N H (1990) The Cauliflower Mosaic Virus-35s Promoter-Combinatorial Regulation of Transcription in Plants. Science 250: 959-966

Ennajdaoui H, Vachon G, Giacalone C, Besse I, Sallaud C, Herzog M, Tissier A (2010) Trichome specific expression of the tobacco (*Nicotiana sylvestris*) cembratrien-ol synthase genes is controlled by both activating and repressing cis-regions. Plant Molecular Biology 73: 673-685

Hillen L W, Pollard G, Wake L V, White N (1982) Hydrocracking Of The Oils Of *Botryococcus-braunii* To Transport Fuels. Biotechnology And Bioengineering 24: 193-205

Niehaus, Tom, Identification of unique mechanisms for triterpene biosynthesis in *Botryococcus braunii*, PNAS, 12260-12265

Verdaguer B, deKochko A, Beachy R N, Fauquet C (1996) Isolation and expression in transgenic tobacco and rice plants, of the cassava vein mosaic virus (CVMV) promoter. Plant Molecular Biology 31: 1129-1139

Wagner G J, Wang E, Shepherd R W (2004) New approaches for studying and exploiting an old protuberance, the plant trichome. Annals of Botany 93: 3-11

Wang E M, Gan S S, Wagner G J (2002) Isolation and characterization of the CYP71D16 trichome-specific promoter from *Nicotiana tabacum* L. Journal of Experimental Botany 53: 1891-1897

Wu S Q, Schalk M, Clark A, Miles R B, Coates R, Chappell J (2006) Redirection of cytosolic or plastidic isoprenoid precursors elevates terpene production in plants. Nature Biotechnology 24: 1441-1447

INCORPORATION BY REFERENCE

All publications, patents, and patent applications mentioned in this specification are herein incorporated by reference to the same extent as if each individual publication, patent, or patent application was specifically and individually indicated to be incorporated by reference.

It will be understood that various details of the presently disclosed subject matter can be changed without departing from the scope of the subject matter disclosed herein. Furthermore, the foregoing description is for the purpose of illustration only, and not for the purpose of limitation.

Sequences

```
DNA sequences for directing trichome specific
expression pCBTS 1.7 KB: (SEQ ID NO.: 1)
AAAGAGGTGAAACCTAATCTAGTATGCAAACCATGTTAAATTCTCAATT
GTTTTGATAGATAATGAGTTTTCTGATAATTAATAAATTATTAGATAAT
TAAAGGACCAAATTTATATGACTTTTGTTTTTTATCATCTTGATCATAT
ATACAATGTAATGGATACAAGCTTATAGTTGTATAAATTCTATATAATT
AGTTATTCATACATTAATTAGATATATTCAATTGTTCTTTATAAATATA
ATTCAAACCTGAAAGCAATACTTATTTTGTAAGAATTGCAATATTGTTA
TTTTGTTATGGACTTAAATATTAACCATGTTATAATCTTAAGTTTATAT
TATTAGAAAAACTTAGTTTTTGAAAGACTAATATGAACATTAGTACTTA
TTTCAAAAATAAGCGCTTAGATATATGAAATTACTTTAAGTACTTATTT
AAAATAATTAAGTACCACACATACATACATATCTCTACAAACTGTTAAA
GTTTTCTATATGAGTACTTATTTTAAAATAAGAGCATAAATATAATAAA
TTATGTTAAATTCTTATTTAAAATAATAAAGGACCAAACATGCATAAAA
TAAAGTATGAGCTTAATAAGTCAAGAAGCTAATTGATAAGCATTGATGC
CAAATGCACTTACTAACTGTTCTATATTGTAGGAAAAATCTAACTTTTA
TATTAAAAATTTATTTTCATAAAACTTCCCTAATTTTTGAACAAAATCT
TATATTGATTTTTTTAATCAAAGCCAAAATATTTATTTAACTATGAAAA
TTTTTTAACAACTAATTTATTATGGTAAATAATATTGATATGGTAACTT
TCAGCACATGACAAAAATTATAACTAACTGCAGAAGTTTACTGTCTCTC
TGAATCTTGTGGCTATGTCATTCTATCATAACAAATACTTGTAGCTAAT
ACGCCAACGATGTTCTCGATTTCATATAATTTGAATTTTAAAATAGCTT
TTAAATTTAATATTTATTTCAAATCATTATTGTGACTAACATGTTATAA
CCGCAGTAATATTTGGAGATGCAATACTTATATTTAGCTACAAAATTTT
ATTGTATCATAATAAGTTTGTAGCTATTAAGTTAGTTTTTGCCACAAAT
TTTTATAATTGAAGCAAAAATACCTATTCAACTACAATATTTTGTATCG
AGTAATATTTTGTGACTAGAAGATTAATATTATTACAGTAATTTCTGAC
GTGTGGCAAAAACTCATAATTATCTACAAAATATTGTCGTAGCAATAAT
TTTTTATATCTATTAATCCAATTATTGCTACATGCTTTTATAACTTGAG
GCAAAAATATCTATTTAGCTATAACATTTTGTTAGAAGTAATTTTTGTG
ACTATAAAGTTGTTATTGCTACAGTAATTTCAAATGCGTGGCAAAAAAA
ATACGATTAGCTACGAAATTTTATTGTAGCAATAAATTTGTAGCTATTT
GGGTAATATTGCTACGACAGTTAGCAATTATAGCAAAAATGCTAAATCA
GCTTTGTCGATTTAATTTTGTAGCTAATTTTTTTATGAATTTGTAAATA
GCTATGAAATTTTAATTTTTGTGGCTATTGTTAGGTATTAGCCACATAT
AGCTAAGAATTTGTAGCTATATATACATAATGTTGTAGTGGCAAATTCT
AACATTGTAAGCTTGGCTGCCTTTTTTTTTTTGGGCTACAAAACTCT
AAAGTAAAGGAACTAGAAAACTCGTTTGGCGAGAGAAAGAG PCYP16 1.8 Kb: (SEQ ID NO.: 2)
TAAGTTGATAAAGCTAATTTCTCATTTTAGCTACCATCGCTAGTAATCG
TGGCAATAACTACCCTAACTATAGCATTTATTGCTACCAAATAAAATTT
GGCAGCTAATCATAATTTTTTGTCATGAATCAATAGTTATTGTAGCAAT
AGTTATCTCTTAGCCACAATAAATTATTAAAATAAAATATTATAGCTA
AATAAATATTTTTGCTTTAAGTTCTAAAAGGTTGTGGCAATAGTTAAAT
GATATAGTCACAGATTTATTGGTATAATTGAATTATGTTGCTAATTTCT
TAGTTTTTTGCCACGAGTTAAAAATTACCAATAGCTATAGTAACTTTTT
AATCACAATAAAATATTTGAAAGAAAATATTGTAGCTAAATGAATATTT
TTTCCTTCAAGTTATTAAAAGTTGTGGCAATATAGGTTAAATTAGCCAC
ATGTTTCTTGCTTTAATAGAATTTTGTAGCTAATCATTAACTTTTACCA
CGAGTTGAACTTAATATAACAACAATAACCTTTTAACCATAATAAAGCG
```

```
ATTTAAATCAAATATTACTAAATAAATAACTTTGCTTTCAAGTTTCTAT
AAAATCATGGCAATAGTCATTACGATAAAATGATATAACCACGAATATA
TTGCAACGATAAATTCTGTAACTAATCATTAGTTTTTGCGACGAGGTAA
ATTTTCCGTCACAGTAGCAATCTTCTAGGCACATTAAAAATTTGAAACA
AAATTTTGTAGTCAAATAAATATTTATCTTCTTATTTTAAGAAAATAAA
AATAGTTAGATAATAGTTACTACTATTTGTCATGAAAATATCAATAGAT
ACAAATTTAAAGTGACTATAAATTTACGAGTTTACTATACTTTAGTCGT
ACAGTTTGCAATAATAGTATTTTAACCACAATTAGTTATATGTACAAAA
TAACATAAGTGAATAACTTTTTTTCAATGAGAAAATAAGAGTTGCTCAA
ACAATATCAAGTTACAAAAATTTAATTTTAACTGTAAAAGTTATATTTT
TCCAAAATAACATAAACTATAGTAATTATATATAGTTTGAAGTATTAAT
AAAATTTAAATATGCAAAAGTTAATTTTAATAAACCATTTGTATGCCTA
ACTTGTAGCCTCTAAACTATTTTATTTGCTTTATTTATCAAACTCATAT
TTTATTTTATTGCACCTTGTTAGTTTTGGACGTTAATTATATATATTTG
GTGTAAAATTTAAAATATATTAACATTTGTGGAGAATTTATGTATGCCT
GGTTCTTAACTATTTTTTTTTATATAACTGGTTAGAGTAATTTCTTATA
TTTCAGTATTTATTTTTAAATAAGTCCTCATAAATTGAAGACTTTAAAA
GTTTTTGTGTCATTCCTCTTTTTATTTAAGAAATTGAAGAATTCCGCTA
AATTTCATATTTCCGCTGTTATTTAACTGTTTATTTCCCTTGTTAATAT
AATTGGTAAGAAGTTTTAAAATAAAGGAGTTAATGATTTTCTAGGTTCA
TGGCTTGCCTAGCTTCTACGAGTAAGCGCCATCACGACTCCCGAGGATA
AGGAAATCCGGGTCGTAGCATTCACTCACAAAAATTACTAAAAACAAAG
TTTACCCTTCTCCCAAAAGTAAATTTCATATTTGGCTCCACATAATGTG
TTCAATGAGTCAAGTGAAGTACTTTTCATGACAAAAAAAAGTTGCTGAA
AAATGCATATCTCATATTTTTTTTTAGAGAAATCCATTTCTTGCCTAA
ACGAAAGCCTATAAAAGAGCATATATTGCAACAACAGTTTGCAGAAACT
ATCAAGTCAAATAATCCCCCCTTTAATTCCCTCCCAAA
```

35S CAMV double enhancer element-2Xe35S: (SEQ ID NO: 3)

```
AATGACAAGAAGAAAATCTTCGTCAACATGGTGGAGCACGACACGCTTG
TCTACCTCCAAAAATATCAAAGATACAGTCTCAGAAGACCAAAGGGAAT
TGAGACTTTTCAACAAAGGGTAATATCCGGAAACCTCCTCGGATTCCAT
TGCCCAGCTATCTGTCACTTTATTGTGAAGATAGTGGAAAAGGAAGGTG
GCTCCTACAAATGCCATCATTGCGATAAAGGAAAGGCCATCGTTGAAGA
TGCCTCTGCCGACAGTGGTCCCAAAGATGGACCCCCACCCACGAGGAGC
ATCGTGGAAAAGAAGACGTTCCAACCACGTCTTCAAAGCAAGTGGATT
GATGTGATACATGGTGGAGCACGACACGCTTGTCTACCTCCAAAAATA
TCAAAGATACAGTCTCAGAAGACCAAAGGGAATTGAGACTTTTCAACAA
AGGGTAATATCCGGAAACCTCCTCGGATTCCATTGCCCAGCTATCTGTC
ACTTTATTGTGAAGATAGTGGAAAAGGAAGGTGGCTCCTACAAATGCCA
TCATTGCGATAAAGGAAAGGCCATCGTTGAAGATGCCTCTGCCGACAGT
GGTCCCAAAGATGGACCCCCACCCACGAGGAGCATCGTGGAAAAGAAG
ACGTTCCAACCACGTCTTCAAAGCAAGTGGATTGATGTGATATCTCCAC
TGACGTAAGGGATGACGCAC
```

DNA Sequences for Directing Constitutive Gene Expression

35S CAMV promoter (Pca)—previously described by Benfey and Chua [Benfey, 1990].

35S Cassava vein mosaic virus promoter (Pcv)—previously described by Verdaguer et al [Verdaguer, 1996], herein incorporated by reference.

DNA sequences for yeast truncated squalene synthase (ySQS):
(SEQ ID NO: 4)

```
ATGGGAAAGCTATTACAATTGGCATTGCATCCGGTCGAGATGAAGGCAGCTTTGAA

GCTGAAGTTTTGCAGAACACCGCTATTCTCCATCTATGATCAGTCCACGTCTCCATA

TCTCTTGCACTGTTTCGAACTGTTGAACTTGACCTCCAGATCGTTTGCTGCTGTGATC

AGAGAGCTGCATCCAGAATTGAGAAACTGTGTTACTCTCTTTTATTTGATTTTAAGG

GCTTTGGATACCATCGAAGACGATATGTCCATCGAACACGATTTGAAAATTGACTTG

TTGCGTCACTTCCACGAGAAATTGTTGTTAACTAAATGGAGTTTCGACGGAAATGCC

CCCGATGTGAAGGACAGAGCCGTTTTGACAGATTTCGAATCGATTCTTATTGAATTC

CACAAATTGAAACCAGAATATCAAGAAGTCATCAAGGAGATCACCGAGAAAATGG

GTAATGGTATGGCCGACTACATCTTAGATGAAAATTACAACTTGAATGGGTTGCAAA

CCGTCCACGACTACGACGTGTACTGTCACTACGTAGCTGGTTTGGTCGGTGATGGTT

TGACCCGTTTGATTGTCATTGCCAAGTTTGCCAACGAATCTTTGTATTCTAATGAGCA

ATTGTATGAAAGCATGGGTCTTTTCCTACAAAAAACCAACATCATCAGAGATTACAA

TGAAGATTTGGTCGATGGTAGATCCTTCTGGCCCAAGGAAATCTGGTCACAATACGC

TCCTCAGTTGAAGGACTTCATGAAACCTGAAAACGAACAACTGGGGTTGGACTGTA

TAAACCACCTCGTCTTAAACGCATTGAGTCATGTTATCGATGTGTTGACTTATTTGGC

CGGTATCCACGAGCAATCCACTTTCCAATTTGTGCCATTCCCCAAGTTATGGCCATT

GCAACCTTGGCTTTGGTATTCAACAACCGTGAAGTGCTACATGGCAATGTAAAGATT

CGTAAGGGTACTACCTGCTATTTAATTTTGAAATCAAGGACTTTGCGTGGCTGTGTC

GAGATTTTTGACTATTACTTACGTGATATCAAATCTAAATTGGCTGTGCAAGATCCA

AATTTCTTAAAATTGAACATTCAAATCTCCAAGATCGAACAGTTTATGGAAGAAATG

TACCAGGATAAATTACCTCCTAACGTGAAGCCAAATGAAACTCCAATTTTCTTGAAA
```

-continued

```
GTTAAAGAAAGATCCAGATACGATGATGAATTGGTTCCAACCCAACAAGAAGAAGA

GTACAAGTTCAATATGGTTTTATCTATCATCTTGTCCGTTCTTCTTGGGTTTTATTATA

TATACACTTTACACAGAGCGTGA

DNA sequence for avian farnesyl diphosphate synthase (FPS):
                                                (SEQ ID NO: 5)
ATGCAGCCCCATCATCATCATAAAGAGGGGCGTATGCATAAATTTACTGGTGTCAAT

GCCAAGTTTCAGCAACCCGCGTTGAGGAACCTCAGCCCCGTGGTGGTTGAGAGGGA

GAGGGAGGAGTTCGTGGGGTTCTTCCCGCAGATCGTCCGCGATCTGACCGAGGACG

GCATCGGACACCCGGAGGTGGGCGACGCTGTGGCGCGGCTGAAGGAGGTGCTGCAA

TACAACGCTCCCGGTGGGAAATGCAATCGTGGGCTGACGGTGGTGGCTGCGTACCG

GGAGCTGTCGGGGCCGGGGCAGAAGGATGCTGAGAGCCTGCGGTGCGCGCTGGCCG

TGGGTTGGTGCATCGAGTTGTTCCAGGCCTTCTTCCTGGTGGCTGATGATATCATGG

ATCAGTCCCTCACGCGCCGGGGGCAGCTGTGTTGGTATAAGAAGGAGGGGGTCGGT

TTGGATGCCATCAACGACTCCTTCCTCCTCGAGTCCTCTGTGTACAGAGTGCTGAAG

AAGTACTGCAGGCAGCGGCCGTATTACGTGCATCTGTTGGAGCTCTTCCTGCAGACC

GCCTACCAGACTGAGCTCGGGCAGATGCTGGACCTCATCACAGCTCCCGTCTCCAAA

GTGGATTTGAGTCACTTCAGCGAGGAGAGGTACAAAGCCATCGTTAAGTACAAGAC

TGCCTTCTACTCCTTCTACCTACCCGTGGCTGCTGCCATGTATATGGTTGGGATCGAC

AGTAAGGAAGAACACGAGAATGCCAAAGCCATCCTGCTGGAGATGGGGGAATACTT

CCAGATCCAGGATGATTACCTGGACTGCTTTGGGGACCCGGCGCTCACGGGGAAGG

TGGGCACCGACATCCAGGACAATAAATGCAGCTGGCTCGTGGTGCAGTGCCTGCAG

CGCGTCACGCCGGAGCAGCGGCAGCTCCTGGAGGACAACTACGGCCGTAAGGAGCC

CGAGAAGGTGGCGAAGGTGAAGGAGCTGTATGAGGCCGTGGGGATGAGGGCTGCG

TTCCAGCAGTACGAGGAGAGCAGCTACCGGCGCCTGCAGGAACTGATAGAGAAGCA

CTCGAACCGCCTCCCGAAGGAGATCTTCCTCGGCCTGGCACAGAAGATCTACAAAC

GCCAGAAATGA
```

The DNA sequence corresponding to the plastid targeting (tp)
signal sequence is noted in italic letters and the linker
sequence (underlined) plus the first codon for the gene
fusion (normal font). The fusion genes were either for
ySQS or FPS-see above. (SEQ ID NO: 6)

```
ATGGCTTCCTCTATGCTCTCCTCCGCCGCTGTGGTTACATCCCCGGCTCAGGCCACCATG

GTCGCTCCATTCACCGGCTTGAAGTCATCCGCTGCATTCCCGGTCACCCGCAAGACCAAC

AAGGACATCACTTCCATCGCAAGCAACGGGGGAAGATCTAGCTGCATGAAGACTAGTAT

G
```

Either of the Two FPP Synthases Found in *Arabidopsis*

```
FPS 2 protein
>gi|13431525|sp|Q43315.1|FPPS2_ARATH RecName: Full = Farnesyl
pyrophosphate synthase 2; Short = FPP synthase 2; Short = FPS
2; AltName: Full = (2E,6E)-farnesyl diphosphate synthase 2;
AltName: Full = Dimethylallyltranstransferase 2; AltName:
Full = Farnesyl diphosphate synthase 2; AltName: Full =
Geranyltranstransferase 2
                                                (SEQ ID NO: 7)
MADLKSTFLDVYSVLKSDLLQDPSFEFTHESRQWLERMLDYNVRGGKLNRGLSVVDSY

KLLKQGQDLTEKETFLSCALGWCIEWLQAYFLVLDDIMDNSVTRRGQPCWFRKPKVG

MIAINDGILLRNHIHRILKKHFREMPYYVDLVDLFNEVEFQTACGQMIDLITTFDGEKDL
```

-continued

```
SKYSLQIHRRIVEYKTAYYSFYLPVACALLMAGENLENHTDVKTVLVDMGIYFQVQDD

YLDCFADPETLGKIGTDIEDFKCSWLVVKALERCSEEQTKILYENYGKAEPSNVAKVKA

LYKELDLEGAFMEYEKESYEKLTKLIEAHQSKAIQAVLKSFLAKIYKRQK mRNA
                                                      (SEQ ID NO: 8)
AATCAGGTTCCACATTTGGCTTTGCACACCTTCCTTGATCCTATCAATGGCGGATCTG

AAATCAACCTTCCTCGACGTTTACTCTGTTCTCAAGTCTGATCTGCTTCAAGATCCTT

CCTTTGAATTCACCCACGAATCTCGTCAATGGCTTGAACGGATGCTTGACTACAATG

TACGCGGAGGGAAGCTAAATCGTGGTCTCTCTGTGGTTGATAGCTACAAGCTGTTGA

AGCAAGGTCAAGACTTGACGGAGAAAGAGACTTTCCTCTCATGTGCTCTTGGTTGGT

GCATTGAATGGCTTCAAGCTTATTTCCTTGTGCTTGATGACATCATGGACAACTCTGT

CACACGCCGTGGCCAGCCTTGTTGGTTTAGAAAGCCAAAGGTTGGTATGATTGCCAT

TAACGATGGGATTCTACTTCGCAATCATATCCACAGGATTCTCAAAAAGCACTTCAG

GGAAATGCCTTACTATGTTGACCTCGTTGATTTGTTTAACGAGGTAGAGTTTCAAAC

AGCTTGCGGCCAGATGATTGATTTGATCACCACCTTTGATGGAGAAAAGATTTGTC

TAAGTACTCCTTGCAAATCCATCGGCGTATTGTTGAGTACAAAACAGCTTATTACTC

ATTTTATCTTCCTGTTGCTTGCGCATTGCTCATGGCGGGAGAAAATTTGGAAAACCA

TACTGATGTGAAGACTGTTCTTGTTGACATGGGAATTTACTTTCAAGTACAGGATGA

TTATCTGGACTGTTTTGCTGATCCTGAGACACTTGGCAAGATAGGGACAGACATAGA

AGATTTCAAATGCTCCTGGTTGGTAGTTAAGGCATTGGAACGCTGCAGTGAAGAAC

AAACTAAGATACTATACGAGAACTATGGTAAAGCCGAACCATCAAACGTTGCTAAG

GTGAAAGCTCTCTACAAAGAGCTTGATCTCGAGGGAGCGTTCATGGAATATGAGAA

GGAAAGCTATGAGAAGCTGACAAAGTTGATCGAAGCTCACCAGAGTAAAGCAATTC

AAGCAGTGCTAAAATCTTTCTTGGCTAAGATCTACAAGAGGCAGAAGTAGAGACAT

ACTCGGGCCTCTCTCCGTTTTATTCTTCTGACATTTATGTATTGGTGCATGACTTCTTT

TGCCTTAGATCTTATGTTCCCTTCCGAAAATAGAATTTGAGATTCTTGTTCATGCTTA

TAGTATAGAGACTTAGAAAATGTCTATGTTTCTTTTAATTTCTGAATAAAAAATGTG

CAATCAGTGAT

FPS 1 protein
>gi|21431776|sp|Q09152.2|FPPS1_ARATH RecName: Full = Farnesyl
pyrophosphate synthase 1, mitochondrial; Short = FPP synthase
1; Short = FPS 1; AltName: Full = (2E,6E)-farnesyl diphosphate
synthase 1; AltName: Full = Dimethylallyltranstransferase 1;
AltName: Full = Farnesyl diphosphate synthase 1; AltName:
Full = Geranyltranstransferase 1; Flags: Precursor
                                                      (SEQ ID NO: 9)
MSVSCCCRNLGKTIKKAIPSHHLHLRSLGGSLYRRRIQSSSMETDLKSTFLNVYSVLKSD

LLHDPSFEFTNESRLWVDRMLDYNVRGGKLNRGLSVVDSFKLLKQGNDLTEQEVFLSC

ALGWCIEWLQAYFLVLDDIMDNSVTRRGQPCWFRVPQVGMVAINDGILLRNHIHRILK

KHFRDKPYYVDLVDLFNEVELQTACGQMIDLITTFEGEKDLAKYSLSIHRRIVQYKTAY

YSFYLPVACALLMAGENLENHIDVKNVLVDMGIYFQVQDDYLDCFADPETLGKIGTDIE
```

-continued

DFKCSWLVVKALERCSEEQTKILYENYGKPDPSNVAKVKDLYKELDLEGVFMEYES

KSYEKLTGAIEGHQSKAIQAVLKSFLAKIYKRQK mRNA
(SEQ ID NO: 10)
ATGAGTGTGAGTTGTTGTTGTAGGAATCTGGGCAAGACAATAAAAAAGGCAATACC

TTCACATCATTTGCATCTGAGAAGTCTTGGTGGGAGTCTCTATCGTCGTCGTATCCA

AAGCTCTTCAATGGAGACCGATCTCAAGTCAACCTTTCTCAACGTTTATTCTGTTCTC

AAGTCTGACCTTCTTCATGACCCTTCCTTCGAATTCACCAATGAATCTCGTCTCTGGG

TTGATCGGATGCTGGACTACAATGTACGTGGAGGGAAACTCAATCGGGGTCTCTCTG

TTGTTGACAGTTTCAAACTTTTGAAGCAAGGCAATGATTTGACTGAGCAAGAGGTTT

TCCTCTCTTGTGCTCTCGGTTGGTGCATTGAATGGCTCCAAGCTTATTTCCTTGTGCT

TGATGATATTATGGATAACTCTGTCACTCGCCGTGGTCAACCTTGCTGGTTCAGAGT

TCCTCAGGTTGGTATGGTTGCCATCAATGATGGGATTCTACTTCGCAATCACATCCA

CAGGATTCTCAAAAAGCATTTCCGTGATAAGCCTTACTATGTTGACCTTGTTGATTTG

TTTAATGAGGTTGAGTTGCAAACAGCTTGTGGCCAGATGATAGATTTGATCACCACC

TTTGAAGGAGAAAAGGATTTGGCCAAGTACTCATTGTCAATCCACCGTCGTATTGTC

CAGTACAAAACGGCTTATTACTCATTTTATCTCCCTGTTGCTTGTGCGTTGCTTATGG

CGGGCGAAAATTTGGAAAACCATATTGACGTGAAAAATGTTCTTGTTGACATGGGA

ATCTACTTCCAAGTGCAGGATGATTATCTGGATTGTTTTGCTGATCCCGAGACGCTT

GGCAAGATAGGAACAGATATAGAAGATTTCAAATGCTCGTGGTTGGTGGTTAAGGC

ATTAGAGCGCTGCAGCGAAGAACAAACTAAGATATTATATGAGAACTATGGTAAAC

CCGACCCATCGAACGTTGCTAAAGTGAAGGATCTCTACAAAGAGCTGGATCTTGAG

GGAGTTTTCATGGAGTATGAGAGCAAAAGCTACGAGAAGCTGACTGGAGCGATTGA

GGGACACCAAAGTAAAGCAATCCAAGCAGTGCTAAAATCCTTCTTGGCTAAGATCT

ACAAGAGGCAGAAGTAG

The yeast (Saccharomyces cerevisiae) FPP Synthase, also
known as the ERG 20 gene
>gi|120479|sp|P08524.2|FPPS_YEAST RecName: Full = Farnesyl
pyrophosphate synthase; Short = FPP synthase; Short = FPS;
AltName: Full = (2E,6E)-farnesyl diphosphate synthase;
AltName: Full = Dimethylallyltranstransferase; AltName:
Full = Farnesyl diphosphate synthase; AltName: Full =
Geranyltranstransferase
(SEQ ID NO: 11)
MASEKEIRRERFLNVFPKLVEELNASLLAYGMPKEACDWYAHSLNYNTPGGKLNRGLS

VVDTYAILSNKTVEQLGQEEYEKVAILGWCIELLQAYFLVADDMMDKSITRRGQPCWY

KVPEVGEIAINDAFMLEAAIYKLLKSHFRNEKYYIDITELFHEVTFQTELGQLMDLITAPE

DKVDLSKFSLKKHSFIVTFKTAYYSFYLPVALAMYVAGITDEKDLKQARDVLIPLGEYF

QIQDDYLDCFGTPEQIGKIGTDIQDNKCSWVINKALELASAEQRKTLDENYGKKDSVAE

AKCKKIFNDLKIEQLYHEYEESIAKDLKAKISQVDESRGFKADVLTAFLNKVYKRSK mRNA
(SEQ ID NO: 12)
ATGGCTTCAGAAAAAGAAATTAGGAGAGAGAGATTCTTGAACGTTTTCCCTAAATT

AGTAGAGGAATTGAACGCATCGCTTTTGGCTTACGGTATGCCTAAGGAAGCATGTG

ACTGGTATGCCCACTCATTGAACTACAACACTCCAGGCGGTAAGCTAAATAGAGGT

TTGTCCGTTGTGGACACGTATGCTATTCTCTCCAACAAGACCGTTGAACAATTGGGG

CAAGAAGAATACGAAAAGGTTGCCATTCTAGGTTGGTGCATTGAGTTGTTGCAGGCT

-continued

```
TACTTCTTGGTCGCCGATGATATGATGGACAAGTCCATTACCAGAAGAGGCCAACC

ATGTTGGTACAAGGTTCCTGAAGTTGGGGAAATTGCCATCAATGACGCATTCATGTT

AGAGGCTGCTATCTACAAGCTTTTGAAATCTCACTTCAGAAACGAAAAATACTACAT

AGATATCACCGAATTGTTCCATGAGGTCACCTTCCAAACCGAATTGGGCCAATTGAT

GGACTTAATCACTGCACCTGAAGACAAAGTCGACTTGAGTAAGTTCTCCCTAAAGA

AGCACTCCTTCATAGTTACTTTCAAGACTGCTTACTATTCTTTCTACTTGCCTGTCGC

ATTGGCCATGTACGTTGCCGGTATCACGGATGAAAAGGATTTGAAACAAGCCAGAG

ATGTCTTGATTCCATTGGGTGAATACTTCCAAATTCAAGATGACTACTTAGACTGCTT

CGGTACCCCAGAACAGATCGGTAAGATCGGTACAGATATCCAAGATAACAAATGTT

CTTGGGTAATCAACAAGGCATTGGAACTTGCTTCCGCAGAACAAAGAAAGACTTTA

GACGAAAATTACGGTAAGAAGGACTCAGTCGCAGAAGCCAAATGCAAAAAGATTTT

CAATGACTTGAAAATTGAACAGCTATACCACGAATATGAAGAGTCTATTGCCAAGG

ATTTGAAGGCCAAAATTTCTCAGGTCGATGAGTCTCGTGGCTTCAAAGCTGATGTCT

TAACTGCGTTCTTGAACAAAGTTTACAAGAGA AGCAAATAG
```

The human FPP synthase
>gi|215274250|sp|P14324.4|FPPS_HUMAN RecName: Full = Farnesyl pyrophosphate synthase; Short = FPP synthase; Short = FPS; AltName: Full = (2E,6E)-farnesyl diphosphate synthase; AltName: Full = Dimethylallyltranstransferase; AltName: Full = Farnesyl diphosphate synthase; AltName: Full = Geranyltranstransferase (SEQ ID NO: 13)

```
MPLSRWLRSVGVFLLPAPYWAPRERWLGSLRRPSLVHGYPVLAWHSARCWCQAWTEE

PRALCSSLRMNGDQNSDVYAQEKQDFVQHFSQIVRVLTEDEMGHPEIGDAIARLKEVLE

YNAIGGKYNRGLTVVVAFRELVEPRKQDADSLQRAWTVGWCVELLQAFFLVADDIMD

SSLTRRGQICWYQKPGVGLDAINDANLLEACIYRLLKLYCREQPYYLNLIELFLQSSYQT

EIGQTLDLLTAPQGNVDLVRFTEKRYKSIVKYKTAFYSFYLPIAAAMYMAGIDGEKEHA

NAKKILLEMGEFFQIQDDYLDLFGDPSVTGKIGTDIQDNKCSWLVVQCLQRATPEQYQ

ILKENYGQKEAEKVARVKALYEELDLPAVFLQYEEDSYSHIMALIEQYAAPLPPAVFLG

LARKIYKRRK
``` mRNA (SEQ ID NO: 14)

```
ATGCCCCTGTCCCGCTGGTTGAGATCTGTGGGGGTCTTCCTGCTGCCAGCCCCCTAC

TGGGCACCCCGGGAGAGGTGGCTGGGTTCCCTACGGCGGCCCTCCCTGGTGCACGG

GTACCCAGTCCTGGCCTGGCACAGTGCCCGCTGCTGGTGCCAAGCGTGGACAGAGG

AACCTCGAGCCCTTTGCTCCTCCCTCAGAATGAACGGAGACCAGAATTCAGATGTTT

ATGCCCAAGAAAAGCAGGATTTCGTTCAGCACTTCTCCCAGATCGTTAGGGTGCTGA

CTGAGGATGAGATGGGGCACCCAGAGATAGGAGATGCTATTGCCCGGCTCAAGGAG

GTCCTGGAGTACAATGCCATTGGAGGCAAGTATAACCGGGGTTTGACGGTGGTAGT

AGCATTCCGGGAGCTGGTGGAGCCAAGGAAACAGGATGCTGATAGTCTCCAGCGGG

CCTGGACTGTGGGCTGGTGTGTGGAACTGCTGCAAGCTTTCTTCCTGGTGGCAGATG

ACATCATGGATTCATCCCTTACCCGCCGGGGACAGATCTGCTGGTATCAGAAGCCGG

GCGTGGGTTTGGATGCCATCAATGATGCTAACCTCCTGGAAGCATGTATCTACCGCC

TGCTGAAGCTCTATTGCCGGGAGCAGCCCTATTACCTGAACCTGATCGAGCTCTTCC

TGCAGAGTTCCTATCAGACTGAGATTGGGCAGACCCTGGACCTCCTCACAGCCCCCC
```

-continued

```
AGGGCAATGTGGATCTTGTCAGATTCACTGAAAAGAGGTACAAATCTATTGTCAAGT

ACAAGACAGCTTTCTACTCCTTCTACCTTCCTATAGCTGCAGCCATGTACATGGCAG

GAATTGATGGCGAGAAGGAGCACGCCAATGCCAAGAAGATCCTGCTGGAGATGGG

GGAGTTCTTTCAGATTCAGGATGATTACCTTGACCTCTTTGGGGACCCCAGTGTGAC

CGGCAAAATTGGCACTGACATCCAGGACAACAAATGCAGCTGGCTGGTGGTTCAGT

GTCTGCAACGGGCCACTCCAGAACAGTACCAGATCCTGAAGGAAAATTACGGGCAG

AAGGAGGCTGAGAAAGTGGCCCGGGTGAAGGCGCTATATGAGGAGCTGGATCTGCC

AGCAGTGTTCTTGCAATATGAGGAAGACAGTTACAGCCACATTATGGCTCTCATTGA

ACAGTACGCAGCACCCCTGCCCCCAGCCGTCTTTCTGGGGCTTGCGCGCAAAATCTA

CAAGCGGAGAAAGTGA
```

The FPP synthase from an alga, *Chlamydomonas reinhardtii*
>gi|158277426|gb|EDP03194.1|farnesyl diphosphate synthase
[*Chlamydomonas reinhardtii*]

(SEQ ID NO: 15)
```
MSGEPTPKKMKATYVHDRENFTKVYETLRDELLNDDCLSPAGSPQAQAAQEWFKEVN

DYNVPGGKLNRGMAVYDVLASVKGPDGLSEDEVFKANALGWCIEWLQAFFLVADDIM

DGSITRRGQPCWYKQPKVGMIACNDYILLECCIYSILKRHFRGHAAYAQLMDLFHETTF

QTSHGQLLDLTTAPIGSVDLSKYTEDNYLRIVTYKTAYYSFYLPVACGMVLAGITDPAA

FDLAKNICVEMGQYFQIQDDYLDCYGDPEVIGKIGTDIEDNKCSWLVCTALKIATEEQK

EVIKANYGHKEAESVAAIKALYVELGIEQRFKDYEAASYAKLEGTISEQTLLPKAVFTS

LLAKIYKRKK
``` mRNA (SEQ ID NO: 16)
```
ATGAGCGGCGAGCCTACCCCCAAAAAGATGAAGGCCACTTACGTGCACGACCGCGA

GAACTTTACAAAAGTATATGAGACCCTCCGCGATGAGCTCCTGAACGACGACTGCC

TGTCACCCGCCGGCAGTCCTCAGGCTCAGGCCGCGCAGGAGTGGTTCAAGGAGGTG

AACGACTACAACGTGCCGGGCGGCAAGCTGAACCGCGGAATGGCGGTATACGACGT

GCTGGCATCCGTGAAGGGGCCCGACGGTCTATCCGAGGATGAGGTGTTCAAGGCCA

ACGCACTGGGCTGGTGCATCGAGTGGCTGCAAGCGTTCTTCCTGGTGGCGGACGAC

ATCATGGACGGATCCATCACCCGCCGCGGCCAGCCCTGCTGGTACAAGCAGCCCAA

GGTGGGCATGATCGCCTGCAATGACTACATCCTGCTGGAGTGCTGCATCTACTCCAT

CCTCAAGCGCCACTTCCGCGGCCACGCCGCCTATGCGCAGCTGATGGACCTGTTCCA

CGAGACCACGTTCCAGACCAGCCACGGCCAGCTGCTGGACCTGACCACTGCTCCCA

TCGGCTCCGTGGACTTGTCCAAGTACACCGAGGACAACTACCTGCGCATTGTGACCT

ACAAGACCGCCTACTACTCCTTCTACCTGCCCGTGGCGTGCGGCATGGTTCTGGCGG

GCATCACGGACCCGGCCGCCTTCGACCTGGCCAAGAACATTTGTGTGGAGATGGGC

CAGTACTTTCAGATCCAGGATGACTACCTAGACTGCTACGGCGACCCCGAGGTGATT

GGCAAGATTGGTACGGACATCGAGGACAACAAGTGCAGCTGGCTGGTGTGCACGGC

GCTGAAGATTGCCACCGAGGAGCAGAAGGAGGTCATCAAGGCCAACTACGGGCAC

AAGGAGGCTGAGTCGGTGGCCGCCATCAAGGCGCTGTACGTGGAGCTGGGCATTGA

GCAGCGCTTCAAGGACTACGAGGCCGCTTCCTACGCCAAGCTGGAGGGCACCATCT

CGGAGCAGACGCTGCTGCCCAAGGCGGTGTTCACGTCGCTACTGGCCAAGATCTAC

AAGCGCAAGAAGTAA
```

For Triterpenes Synthases

Yeast squalene synthase, carboxy-terminal (3' terminal) truncation (removes membrane spanning domain)

(SEQ ID NO: 17)

atgggaaagctattacaattggcattgcatccggtcgagatgaaggcagctttgaagctgaagttttgcagaacaccgctattctccatctatg
atcagtccacgtctccatatctcttgcactgtttcgaactgttgaacttcacctccagatcgtttgctgctgtgatcagagagctgcatccagaatt
gagaaactgtgttactctcttttatttgattttaagggctttggataccatcgaagacgatatgtccatcgaacacgatttgaaaattgacttgttgc
gtcacttccacgagaaattgttgttaactaaatggagtttcgacggaaatgccccgatgtgaaggacagagccgttttgacagatttcgaatc
gattcttattgaattccacaaattgaaaccagaatatcaagaagtcatcaaggagatcaccgagaaaatgggtaatggtatggccgactacat
cttagatgaaaattacaacttgaatgggttgcaaaccgtccacgactacgacgtgtactgtcactacgtagctggtttggtcggtgatggtttga
cccgtttgattgtcattgccaagtttgccaacgaatctttgtattctaatgagcaattgtatgaaagcatgggtcttttcctacaaaaaaccaacat
catcagagattacaatgaagatttggtcgatggtagatccttctggcccaaggaaatctggtcacaatacgctcctcagttgaaggacttcatg
aaacctgaaaacgaacaactggggttggactgtataaaccacctcgtcttaaacgcattgagtcatgttatcgatgtgttgacttatttggccgg
tatccacgagcaatccactttccaattttgtgccattccccaagttatggccattgcaacctggctttggtattcaacaaccgtgaagctaca
tggcgatgtaaagattcgtaagggtactacctgctgttaatttgaaatcaaggactttgcgtggctgtgtcgagattttgactattacttacgtg
atatcaaatctaaattggctgtgcaagatccaaatttcttaaaattgaacattcaaatctccaagatcgaacagttatggaagaaatgtaccag
gataaaattacctcctaacgtgaagccaaatgaaactccaattttcttgaaagttaaagaaagatccagatacgatgatgaattggttccaaccc
aacaagaagaagagtacaagtga

*Botryococcus braunii* (an alga) Race B squalene synthase, carboxy-terminal truncation (SEQ ID NO: 18)

Atggggatgcttcgctggggagtggagtctttgcagaatccagatgaattaatcccggtcttgaggatgatttatgctgataagtttggaaag
atcaagccaaaggacgaagaccggggcttctgctatgaaattttaaaccttgtttcaagaagttttgcaatcgtcatccaacagctccctgcac
agctgagggacccagtctgcatattttaccttgtactacgcgccctggacacagtcgaagatgatatgaaaattgcagcaaccaccaagattc
ccttgctgcgtgacttttatgagaaaatttctgacaggtcattccgcatgacggccggagatcaaaaagactacatcaggctgttggatcagta
ccccaaagtgacaagcgttttcttgaaattgaccccccgtgaacaagagataattgcagacattacaaagcggatggggaatggaatggct
gacttcgtgcataagggtgttcccgacacagtgggggactacgacctttactgccactatgttgctggggtggtgggtctcgggctttcccag
ttgttcgttgcgagtggactacagtcaccctctttgacccgcagtgaagaccttccaatcacatgggcctcttccttcagaagaccaacatcat
ccgcgactactttgaggacatcaatgagctgcctgccccccggatgttctggcccagagagatctggggcaagtatgcgaacaacctcgct
gagttcaaagacccggccaacaaggcggctgcaatgtgctgcctcaacgagatggtcacagatgcattgaggcacgcggtgtactgcctg
cagtacatgtccatgattgaggatccgcagatcttcaacttctgtgccatccctcagaccatggccttcggcaccctgtctttgtgttacaacaa
ctacactatcttcacagggcccaaagcggctgtgaagctgcgtaggggcaccactgccagctgatgtacacctctaacaatatgtttgcga
tgtaccgtcatttcctcaacttcgcagagaagctttga

*Arabidopsis thaliana* 3' truncated squalene synthase (SEQ ID NO: 19)

Atggggagcttggggacgatgctgagatatccggatgacatatatccgctcctgaagatgaaacgagcgattgagaaagcggagaagca
gatccctcctgagccacactgggggtttctgctattcgatgctccacaaggtttctcgaagcttttctctcgttattcagcaactcaacaccgagct
ccgtaacgccgtgtgtgtgttctacttggttctccgagctcttgatactgttgaggatgatactagcataccaactgatgaaaaggttcccatcct
gatagcttttcaccggcacatatacgatactgattggcattattcatgtggtacgaaggagtacaagattctaatggaccaatttcaccatgtttc
tgcagcttttttggaacttgaaaaagggtatcaagaggctatcgaggaaattactagaagaatgggtgcagggatggccaagtttatctgcca
agaggtagaaactgttgatgactacgatgaatactgccactatgttgctgggcttgttggtttaggtttgtcgaaactcttcctcgctgcaggatc
agaggttttgacaccagattgggaggcgatttccaattcaatggggtttatttctgcagaaaacaaacattatcagagattatcttgaggacatta
atgagataccaaaatcccgcatgttttggcctcgcgagatttggggcaaatgctgacaagcttgaggatttaaaatacgaggagaacaca
aacaaatccgtacagtgcttaaatgaaatggttaccaatgcgttgatgcatattgaagattgcctgaaatacatggtttccttgcgtgatccttcc -continued atatttcggttctgtgccatccctcagatcatggcgattggaacacttgcattatgctataacaatgaacaagtattcagaggcgttgtgaaact gaggcgaggtcttactgctaaagtcattgatcgtacaaagacaatggctgatgtctatggtgctttctatgattttcctgcatgctgtga

*Nicotiana tabacum* 3' truncated squalene synthase (SEQ ID NO: 20)

Atggggagtttgagggctattctgaagaatccagaggatttatatccattggtgaagctgaagctagcggctcgacacgcggagaagcag atcccgccgtctccaaattggggcttctgttactcaatgcttcataaggtttctcgtagctttgctctcgtcattcaacaacttccagtcgagcttc gtgacgccgtgtgcatttctatttggttcttcgagcacttgacactgttgaggatgataccagcattcccaccgatgttaaagttcctattctgat ctcttttcatcagcatgtttatgatcgcgaatggcattttcatgtggtacaaaggagtacaaggttctcatggaccagttccatcatgtatcaact gcttttctggagcttaggaaacattatcagcaggcaattgaggatattaccatgaggatgggtgcaggaatggcaaaattcatatgcaagga ggtggaaacaaccgatgattatgacgaatattgtcactatgtagctgggcttgttgggctaggattgtcaaaactgttccatgcctctgagaaa gaagatctggcttcagattctctctccaactccatgggtttatttcttcagaaaacaaacatcattagagattatttggaagacataaatgaagta cccaagtgccgtatgttctggccccgtgaaatatggagtaaatatgttaacaagcttgaggaattaaagtacgaggataactcggccaaagc agtgcaatgtctaaatgacatggtcactaatgctttatcacatgt Agaagattgtttgacttacatgtctgctttgcgtgatccttccatctttcgattctgtgctattccacaggtcatggcaattgggacattagctatgt gctacgacaacattgaagtcttcagaggagtggtaaaaatgagacgtggtctgactgctaaggtcattgaccggaccaggactattgcagat gtatatggtgcttttttttgacttttcttgtatgctgtga Rat 3' truncated squalene synthase (SEQ ID NO: 21)

Atggagttcgtgaagtgtctaggccacccggaggagttctacaacctgctgcgattccgcatgggaggccggcggaatttcatacccaag atggaccggaactcgctcagcaacagcttgaagacttgctataagtatcttgatcagaccagtcgcagcttcgccgcggttatccaggcgct ggatggggacatacgtcatgcggtgtgtgtgttttacctgatcctccgagccatggacacagtggaggatgacatggccatcagtgtggag aagaagatcccactgctgcgaaactttcacactttcctctatgagccggagtggcggttcaccgagagcaaggagaagcaccgagtagtg ctggaggacttccccacgatctccctggagtttagaaatttggctgagaaatatcaaacagtgatcgctgacatctgtcacaggatgggatgt gggatggcagaatttctaaacaaggatgtaacctccaaacaggactgggacaagtactgtcactatgttgctggactggtgggaatcggcct ttctcgcctattctctgcctcagagtttgaagatcccatagttggtgaagacacagagtgtgccaattctatgggtctgtttctgcagaaaacaa atatcattcgtgattatctggaagaccaacaagaaggaagacagttttggcctcaagaggtatgggcaaatatgttaagaagctggaagac tttgttaagccagagaacgtagatgtggccgtgaagtgcttgaatgaactcataaccaacgccctacaacacatccctgacgtcatcacctac ctgtcaaggctccggaaccaaagtgtgtttaacttctgtgccattccacaggtaatggccattgctacgctggctgcctgttacaataaccatc aggtattcaagggagtagtgaagattcggaaggggcaagcagttaccctcatgatggatgccaccaacatgccagctgtcaaagctatcat ataccagtacatagaagagatttatcaccgggtccccaactcagacccgtcagctagcaaggccaagcagctcatctccaacatcaggacg cagagctga Other Possible Triterpenes Synthases Squalene synthase-like 2 gene from *Botryococcus* (plants
should make and accumulate bisfarnesyl ether).
>gi|342209231|gb|HQ585059.1|*Botryococcus braunii* squalene
synthase-like 2 (SSL-2) mRNA, complete cds (SEQ ID NO: 22)

ATGGTGAAACTCGTCGAGGTTTTGCAGCACCCGGACGAGATCGTCCCCATCCTGCAG

ATGTTGCATAAGACCTACCGCGCAAAGCGCAGCTATAAAGACCCTGGTCTGGCCTTT

TGCTACGGAATGTTGCAACGGGTTTCGAGAAGCTTTTCAGTAGTTATACAGCAGCTG

CCTGACGAATTGCGCCATCCAATATGCGTGTTTTATCTTATTCTTCGGGCCCTGGATA

CTGTCGAGGATGACATGAACCTCCCAAATGAAGTTAAAATACCTCTTCTTCGCACCT

TCCATGAACATCTCTTTGACAGGTCGTGGAAGCTCAAATGTGGATATGGACCGTATG

TAGATTTGATGGAGAACTATCCGCTGGTCACGGATGTCTTCCTTACACTCTCTCCAG

-continued

```
GCGCACAGGAGGTAATCCGGGACAGCACGCGCCGCATGGGCAATGGCATGGCCGA
CTTCATTGGCAAGGATGAGGTCCACTCAGTAGCGGAGTATGATCTGTACTGTCACTA
TGTGGCTGGCTTGGTCGGGAGTGCTGTGGCCAAGATTTTTGTGGACAGCGGGCTGGA
GAAGGAGAATCTGGTCGCAGAGGTGGATCTGGCCAACAACATGGGCCAGTTCCTGC
AAAAGACCAACGTTATTCGAGACTACTTGGAGGATATTAATGAAGAACCGGCCCCT
AGGATGTTCTGGCCGCGGGAGATCTGGGGCAAATATGCCCAGGAGCTGGCGGACTT
CAAGGACCCAGCCAATGAGAAAGCGGCGGTACAGTGCCTGAATCACATGGTCACAG
ATGCACTCCGACACTGCGAGATCGGCCTGAACGTGATCCCGCTGTTGCAGAACATTG
GCATCCTCCGCAGCTGCCTCATCCCCGAAGTCATGGGCTTGAGAACCCTGACCTTGT
GTTACAACAATCCTCAAGTCTTCCGAGGGGTGGTGAAGATGCGGAGAGGGGAGACT
GCCAAGCTGTTCATGAGTATCTACGACAAGCGCTCCTTCTACCAAACATATCTCCGA
CTCGCGAACGAGTTGGAAGCAAAATGTAAAGGGGAGGCGAGTGGAGACCCCATGG
TGGCCACAACGCTGAAGCATGTGCACGGAATCCAGAAGTCATGCAAAGCCGCTCTC
AGCAGCAAAGAGCTGCTTGCCAAGTCTGGCTCGGCCCTCACAGACGATCCCGCTAT
CAGGTTGCTGCTGCTGGTGGGAGTCGTGGCCTACTTTGCATACGCATTCAACTTGGG
AGATGTGCGGGGAGAGCACGGGGTGCGGGCTCTGGGCTCCATTCTGGACCTGTCCC
AGAAAGGCTTGGCTGTGGCGAGTGTCGCTCTGCTGCTGCTGGTGCTTCTGGCCAGGA
GCCGCCTTCCCTTGCTCACCTCTGCTTCTTCCAAGCAGTAG

>gi|342209232|gb|AEL16716.1|squalene synthase-like 2
[Botryococcus braunii]
                                             (SEQ ID NO: 23)
MVKLVEVLQHPDEIVPILQMLHKTYRAKRSYKDPGLAFCYGMLQRVSRSFSVVIQQLPD
ELRHPICVFYLILRALDTVEDDMNLPNEVKIPLLRTFHEHLFDRSWKLKCGYGPYVDLM
ENYPLVTDVFLTLSPGAQEVIRDSTRRMGNGMADFIGKDEVHSVAEYDLYCHYVAGLV
GSAVAKIFVDSGLEKENLVAEVDLANNMGQFLQKTNVIRDYLEDINEEPAPRMFWPREI
WGKYAQELADFKDPANEKAAVQCLNHMVTDALRHCEIGLNVIPLLQNIGILRSCLIPEV
MGLRTLTLCYNNPQVFRGVVKMRRGETAKLFMSIYDKRSFYQTYLRLANELEAKCKGE
ASGDPMVATTLKHVHGIQKSCKAALSSKELLAKSGSALTDDPAIRLLLLVGVVAYFAY
AFNLGDVRGE HGVRALGSILDLSQKGLAVASVALLLLVLLARSRLPLLTSASSKQ Squalene synthase-like 1 gene from Botryococcus (plants
should make and accumulate presqualene alcohol).
>gi|342209229|gb|HQ585058.1|Botryococcus braunii squalene
synthase-like 1 (SSL-1) mRNA, complete cds
                                             (SEQ ID NO: 24)
ATGACTATGCACCAAGACCACGGAGTCATGAAAGACCTTGTCAAGCATCCAAATGA
ATTTCCATACTTGCTCCAACTAGCTGCAACAACGTACGGCTCACCGGCTGCACCGAT
CCCCAAGGAACCGGACCGAGCTTTCTGCTACAATACTCTTCACACCGTTTCGAAGGG
GTTCCCCAGATTTGTTATGAGACTTCCGCAGGAACTCCAAGATCCGATATGCATATT
CTACCTCCTGTTGCGAGCACTAGACACGGTGGAGGATGATATGAACCTCAAAAGTG
AGACGAAGATTTCACTCCTACGCGTTTTCCATGAACACTGTTCAGACAGGAACTGGA
GTATGAAAAGTGATTATGGCATATATGCAGATCTGATGGAAAGATTCCCCCTGGTCG
TATCCGTCTTAGAGAAGCTCCCTCCCGCCACACAGCAGACTTTCAGGGAGAATGTCA
AATACATGGGCAATGGCATGGCAGATTTTATTGATAAGCAGATCCTGACAGTGGAT
GAGTACGACCTCTACTGCCACTATGTGGCCGGCAGTTGCGGCATTGCTGTCACCAAG
```

```
GTCATTGTGCAGTTCAACCTTGCCACGCCTGAAGCTGACTCCTACGACTTTTCCAAC

AGTCTGGGCCTCTTGCTTCAGAAGGCCAACATCATCACTGACTACAATGAAGACATC

AATGAAGAGCCCAGGCCCAGGATGTTCTGGCCCCAGGAGATTTGGGGGAAGTACGC

GGAGAAGTTGGCTGACTTCAATGAACCCGAAAATATTGATACAGCCGTGAAGTGCT

TGAACCACATGGTCACAGATGCAATGCGGCACATTGAGCCTTCCCTCAAAGGCATG

GTTTATTTCACAGACAAGACAGTCTTTCGGGCGCTCGCTCTTCTGCTGGTCACAGCC

TTTGGCCATTTGTCCACTTTGTACAACAACCCCAATGTCTTTAAAGAGAAAGTGAGA

CAGCGGAAGGGAAGGATTGCACGGCTGGTCATGTCATCCAGGAATGTACCAGGCCT

CTTCCGTACATGCCTCAAACTCGCAAACAACTTCGAGTCCAGGTGCAAGCAAGAGA

CGGCAAATGATCCCACTGTGGCCATGACTATCAAGCGCTTGCAATCTATTCAAGCTA

CATGCAGAGATGGCCTGGCCAAGTATGACACACCCTCTGGGCTGAAATCTTTCTGCG

C AGCCCCAACTCCCACCAAGTGA
```

>gi|342209230|gb|AEL16715.1|squalene synthase-like 1
[*Botryococcus braunii*]
                                           (SEQ ID NO: 25)
```
MTMHQDHGVMKDLVKHPNEFPYLLQLAATTYGSPAAPIPKEPDRAFCYNTLHTVSKGF

PRFVMRLPQELQDPICIFYLLLRALDTVEDDMNLKSETKISLLRVFHEHCSDRNWSMKS

DYGIYADLMERFPLVVSVLEKLPPATQQTFRENVKYMGNGMADFIDKQILTVDEYDLY

CHYVAGSCGIAVTKVIVQFNLATPEADSYDFSNSLGLLLQKANIITDYNEDINEEPRPRM

FWPQEIWGKYAEKLADFNEPENIDTAVKCLNHMVTDAMRHIEPSLKGMVYFTDKTVFR

ALALLLVTAFGHLSTLYNNPNVFKEKVRQRKGRIARLVMSSRNVPGLFRTCLKLANNFE

SRCKQETANDPTVAMTIKRLQSIQATCRDGLAKYDTPSGLKSFCAAPTPTK
```

Co-expression of SSL-1 and SSL-3 (Below) either as separate
genes or fused via a linker domain to encode for a hybrid
fused protein.
>gi|342209233|gb|HQ585060.1|*Botryococcus braunii* squalene
synthase-like 3 (SSL-3) mRNA, complete cds
                                           (SEQ ID NO: 26)
```
ATGAAACTTCGGGAAGTCTTGCAGCACCCGGGTGAGATTATCCCTCTCCTGCAAATG

ATGGTCATGGCCTACCGCAGGAAGAGGAAGCCTCAAGATCCCAATTTGGCCTGGTG

CTGGGAGACGCTGATTAAAGTTTCGAGAAGTTACGTTCTAGTCATTCAGCAGCTTCC

TGAAGTACTTCAGGACCCTATCTGCGTCAACTATCTTGTTCTTCGAGGCTTGGACAC

ACTGCAGGATGACATGGCAATTCCCGCAGAGAAGCGGGTTCCACTCCTCCTCGACT

ACTACAACCATATTGGAGACATAACTTGGAAGCCGCCTTGCGGATATGGGCAGTAT

GTGGAGCTGATTGAGGAGTATCCAAGGGTGACAAAAGAGTTCTTGAAACTCAACAA

GCAAGATCAGCAGTTTATCACGGACATGTGCATGCGGCTGGGAGCGGAGATGACAG

TATTTCTCAAGAGGGACGTGTTGACAGTTCCTGACTTGGATCTGTATGCCTTCACTA

ATAACGGGCCAGTTGCTATCTGCCTGACCAAGTTATGGGTGGACAGAAAGTTTGCA

GACCCAAAGCTTCTGGACCGGGAGGACCTATCGGGCCACATGGCCATGTTCTTGGG

CAAGATTAACGTCATCCGCGACATCAAGGAGGATGTCTTGGAGGATCCTCCTCGCAT

CTGGTGGCCGAAGGAGATCTGGGGAAAGTACCTCAAGGACCTGAGGGACATCATCA

AGCCTGAGTATAAAAGGAAGCGCTGGCCTGTCTCAATGACATCCTCACAGATGCA

CTGCGCCATATCGAGCCCTGCCTTCAGTACATGGAGATGGTTTGGGACGAGGGCGTT

TTTAAGTTCTGCGCCGTGCCAGAGCTCATGTCCTTGGCTACCATCTCGGTGTGTTACA

ACAATCCGAAGGTCTTCACAGGTGTTGTCAAGATGAGGAGGGGCGAAACAGCAAAG
```

-continued

```
CTGTTTCTGAGCGTAACAAATATGCCAGCTCTGTACAAGAGTTTTTCAGCCATTGCT

GAAGAAATGGAGGCCAAGTGTGTGAGGGAGGATCCCAACTTTGCACTCACAGTCAA

GCGGCTTCAGGATGTCCAGGCGTTATGCAAGGCAGGCCTAGCAAAATCAAATGGAA

AGGTTTCAGCTAAGGGTGCTTAG
```

\>gi|342209234|gb|AEL16717.1| squalene synthase-like 3 [Botryococcus braunii]

(SEQ ID NO: 27)

```
MKLREVLQHPGEIIPLLQMMVAYRRKRKPQDPNLAWCWETLIKVSRSYVLVI

QQLPEVLQDPICVNYLVLRGLDTLQDDMAIPAEKRVPLLLDYYNHIGDITWKPPC

GYGQYVELIEEYPRVTKEFLKLNKQDQQFITDMCMRLGAEMTVFLKRDVLTVP

DLDLYAFTNNGPVAICLTKLWVDRKFADPKLLDREDLSGHMAMFLGKINVIRDI

KEDVLEDPPRIWWPKEIWGKYLKDLRDIIKPEYQKEALACLNDILTDALRHIEPC

LQYMEMVWDEGVFKFCAVPELMSLATISVCYNNPKVFTGVVKMRRGETAKLFL

SVTNMPALYKSFSAIAEEMEAKCVREDPNFALTVKRLQDVQALCKAGLAKSNG

KVSAKGA
```

The invention claimed is:

1. A method of producing an accumulation of non-volatile hydrophobic triterpenes in a plant cell in non-native intracellular locations, said method comprising:
   selecting an isolated nucleic acid encoding a farnesyl diphosphate synthase and an isolated nucleic acid encoding a triterpene synthase, wherein each synthase lacks a hydrophobic transmembrane spanning domain sequence; and
   transforming a plant cell with the isolated nucleic acid encoding a farnesyl diphosphate synthase and the isolated nucleic acid encoding a triterpene synthase,
   wherein the farnesyl diphosphate synthase and/or triterpene synthase is/are controlled by a heterologous promoter and
   wherein the farnesyl diphosphate synthase and triterpene synthase are both directed to chloroplasts or cytoplasm compartment, for triterpene biosynthesis,
   thereby resulting in the production and accumulation of non-volatile hydrophobic triterpene in non-native intracellular locations for the triterpene biosynthesis wherein said accumulation exceeds wild type amounts of triterpene in the plant cell.

2. The method of claim 1, wherein the triterpene synthase is squalene synthase.

3. The method of claim 2, wherein the squalene synthase is selected from the group consisting of squalene synthase from *Saccharomyces cerevisiae*, *Botryococcus*, *Arabidopsis*, *Nicotiana*, and rat.

4. The method of claim 1, wherein the farnesyl diphosphate synthase is an avian farnesyl diphosphate synthase.

5. The method of claim 1, wherein the farnesyl diphosphate synthase is selected from the group consisting of farnesyl diphosphate synthase from avian, *Arabidopsis*, *Saccharomyces cerevisiae*, human and *Chlamydomonas reinhardtii*.

6. The method of claim 1, wherein the plant cell is tobacco.

7. The method of claim 1, wherein the isolated nucleic acid encoding the triterpene synthase comprises co-expression of *Botryococcus braunii* squalene synthase-like 1 (SSL-1) and *Botryococcus braunii* squalene synthase-like 3 (SSL-3) either as separate genes or fused via a linker domain to encode a hybrid fused protein.

8. The method of claim 1, further comprising transforming the plant cell with an isolated nucleic acid encoding a squalene epoxidase and a β-amyrin synthase.

9. The method of claim 1, further comprising transforming the plant cell with an isolated nucleic acid encoding a triterpene methyltransferase.

10. The method of claim 1, further comprising expressing and targeting the farnesyl diphosphate synthase and the triterpene synthase to a chloroplast compartment of the plant cell, thereby enhancing triterpene accumulation.

11. The method of claim 10, wherein the respective nucleic acids encoding farnesyl diphosphate synthase and the triterpene synthase include respective sequences which target the farnesyl diphosphate synthase and the triterpene synthase to the chloroplast compartment of the plant cell.

12. A transgenic plant cell having triterpene production in non-native intracellular locations for the accumulation of non-volatile hydrophobic triterpenes, the plant cell comprising expression of an isolated nucleic acid encoding a farnesyl diphosphate synthase lacking a hydrophobic transmembrane domain sequence, and an isolated nucleic acid encoding a triterpene synthase lacking a hydrophobic transmembrane domain sequence,
   wherein the farnesyl diphosphate synthase and/or triterpene synthase is/are controlled by a heterologous promoter,
   wherein the farnesyl diphosphate synthase and triterpene synthase are both directed to chloroplasts or both directed to a cytoplasm compartment for non-volatile hydrophobic triterpene biosynthesis,
   wherein co-expression of the farnesyl diphosphate synthase and the triterpene synthase increases an amount of non-volatile hydrophobic triterpenes in the plant cell and synthesis occurs in hydrophilic portion of the chloroplasts or the cytoplasm,
   thereby the transgenic plant cell has production of triterpene in a non-native intracellular location for the triterpene biosynthesis wherein said accumulation exceeds wild type amounts of triterpene in the plant cell.

13. The transgenic plant cell of claim 12, wherein the isolated nucleic acids are operably linked to an expression control sequence.

14. The transgenic plant cell of claim 12, wherein the triterpene synthase is squalene synthase.

15. The transgenic plant cell of claim 12, wherein the squalene synthase is selected from the group consisting of *Saccharomyces cerevisiae, Botryococcus, Arabidopsis, Nicotiana*, and rat.

16. The transgenic plant cell of claim 12, further comprising an isolated nucleic acid encoding a squalene epoxidase and a β-amyrin synthase.

17. The transgenic plant cell of claim 12, wherein the farnesyl diphosphate synthase is selected from the group consisting of farnesyl diphosphate synthase from avian, *Arabidopsis, Saccharomyces cerevisiae*, human and *Chlamydomonas reinhardtii*.

18. The transgenic plant cell of claim 12, wherein the isolated nucleic acid encoding the triterpene synthase comprises co-expression of *Botryococcus braunii* squalene synthase-like 1 (SSL-1) and *Botryococcus braunii* squalene synthase-like 3 (SSL-3) either as separate genes or fused via a linker domain to encode a hybrid fused protein.

19. The transgenic plant cell of claim 12, further comprising an isolated nucleic acid encoding a triterpene methyltransferase.

20. The transgenic plant cell of claim 12, wherein the respective nucleic acids encoding farnesyl diphosphate synthase and the triterpene synthase include respective sequences which target the farnesyl diphosphate synthase and the triterpene synthase to the chloroplast compartment of the plant cell.

21. The transgenic plant cell of claim 20, wherein the respective sequences encode N-terminus amino acid sequences of the farnesyl diphosphate synthase and the triterpene synthase have been manipulated with plastid targeting signal sequences which target the farnesyl diphosphate synthase and the triterpene synthase to the chloroplast.

22. A method of increasing triterpene production in a plant cell via triterpene production in non-native locations in the plant cell for the accumulation of triterpenes, said method comprising transforming a plant cell with a first isolated nucleic acid encoding a farnesyl diphosphate synthase lacking a hydrophobic transmembrane domain sequence and a second isolated nucleic acid encoding a triterpene synthase lacking a hydrophobic transmembrane domain sequence, wherein the farnesyl diphosphate synthase and/or triterpene synthase is/are controlled by a heterologous promoter, wherein the farnesyl diphosphate synthase and triterpene synthase are both directed to chloroplasts or both directed to cytoplasm compartment for triterpene biosynthesis, and wherein co-expression of the farnesyl diphosphate synthase and the triterpene synthase increases an amount of non-volatile hydrophobic triterpene in the plant cell produced at non-native intracellular locations for triterpene biosynthesis and synthesis occurs in hydrophilic portion of chloroplasts or cytoplasm, wherein said accumulation exceeds wild type amounts of triterpene in the plant cell.

23. The method of claim 22, wherein the respective nucleic acids encoding farnesyl diphosphate synthase and the triterpene synthase include respective sequences which target the farnesyl diphosphate synthase and the triterpene synthase to the chloroplast compartment of the plant cell.

24. The method of claim 22, wherein the respective sequences encode N-terminus amino acid sequences of the farnesyl diphosphate synthase and the triterpene synthase have been manipulated with plastid targeting signal sequences which target the farnesyl diphosphate synthase and the triterpene synthase to the chloroplast.

25. The transgenic plant cell of claim 12, wherein at least one gene encoding for either FPP synthase or a triterpene synthase, or both are under the control of a promoter which is not native to the plant cell.

26. The transgenic plant cell of claim 12, wherein the FPP synthase and triterpene synthase have been fused with viral promoter elements which provide constitutive transcription of the farnesyl diphosphate synthase and/or triterpene synthase.

27. The transgenic plant cell of claim 12, wherein the triterpene synthase is devoid of native signal sequence protein domains.

28. The transgenic plant cell of claim 27, wherein a native gene sequence encoding a carboxy terminal domain of the triterpene synthase has been manipulated such that signal sequences directing a native triterpene synthase to the endoplasmic reticulum have been removed or significantly altered.

29. The method of claim 1, wherein at least one of the nucleic acid encoding farnesyl diphosphate synthase and the triterpene synthase is under the control of a promoter sequence not native to the plant cell.

30. The method of claim 1, wherein the farnesyl diphosphate synthase and triterpene synthase have been fused with viral promoter elements which provide constitutive transcription of farnesyl diphosphate synthase and triterpene synthase genes.

31. The method of claim 1, wherein the triterpene synthase is devoid of a native signal sequence protein domain(s).

32. The method of claim 31, wherein a native gene sequence encoding a carboxy terminal domain of the triterpene synthase has been manipulated such that signal sequences directing a native triterpene synthase to the endoplasmic reticulum have been removed or altered to thereby result in the triterpene synthase not being directed to the endoplasmic reticulum.

33. The method of claim 1, wherein the isolated nucleic acid encoding a triterpene synthase does not include a sequence encoding a membrane spanning domain, thus resulting in the triterpene synthase not having a membrane spanning domain.

34. The transgenic plant cell of claim 12, wherein the isolated nucleic acid encoding a triterpene synthase does not include a sequence encoding a membrane spanning domain, thus resulting in the triterpene synthase not having a membrane spanning domain.

35. The method of claim 22, wherein the isolated nucleic acid encoding a triterpene synthase does not include a sequence encoding a membrane spanning domain, thus resulting in the triterpene synthase not having a membrane spanning domain.

36. The method of claim 1, wherein the accumulation of the triterpenes is at a total level that exceeds that of a wild plant cell corresponding to said plant cell.

37. The method of claim 36, wherein the amount of the triterpene is at least 100 times that of the wild type cell.

38. The method of claim 1, wherein the amount of triterpene accumulated is in an amount of between 147 and 1760 µg/g.

39. A transgenic plant cell having triterpene production in non-native intracellular locations for the accumulation of non-volatile hydrophobic triterpenes, the plant cell comprising expression of an isolated nucleic acid encoding a farnesyl diphosphate synthase lacking a hydrophobic transmembrane domain sequence, and an isolated nucleic acid encoding a triterpene synthase lacking a hydrophobic transmembrane domain sequence,
- wherein the farnesyl diphosphate synthase and triterpene synthase are both directed to chloroplasts or both directed to a cytoplasm compartment for non-volatile hydrophobic triterpene biosynthesis,
- wherein co-expression of the farnesyl diphosphate synthase and the triterpene synthase increases an amount of non-volatile hydrophobic triterpenes in the plant cell and synthesis occurs in hydrophilic portion of the chloroplasts or the cytoplasm,
- thereby the transgenic plant cell has production of triterpene in a non-native intracellular location for the triterpene biosynthesis wherein said accumulation exceeds wild type amounts of triterpene in the plant cell.

\* \* \* \* \*

SEQUENCE LISTING

<160> NUMBER OF SEQ ID NOS: 27

<210> SEQ ID NO 1
<211> LENGTH: 1756
<212> TYPE: DNA
<213> ORGANISM: Artificial Sequence
<220> FEATURE:
<223> OTHER INFORMATION: sythentic polynucleotide

<400> SEQUENCE: 1

```
aaagaggtga aacctaatct agtatgcaaa ccatgttaaa ttctcaattg ttttgataga      60
taatgagttt tctgataatt aataaattat tagataatta aaggaccaaa tttatatgac     120
ttttgttttt tatcatcttg atcatatata caatgtaatg gatacaagct tatagttgta     180
taaattctat ataattagtt attcatacat taattagata tattcaattg ttctttataa     240
atataattca aacctgaaag caatacttat tttgtaagaa ttgcaatatt gttattttgt     300
tatggactta aatattaacc atgttataat cttaagttta tattattaga aaacttagt      360 ttttgaaaga ctaatatgaa cattagtact tatttcaaaa ataagcgctt agatatatga     420
aattacttta agtacttatt taaaataatt aagtaccaca catacataca tatctctaca     480
aactgttaaa gttttctata tgagtactta ttttaaaata agagcataaa tataataaat     540
tatgttaaat tcttatttaa aataataaag gaccaaacat gcataaaata aagtatgagc     600
ttaataagtc aagaagctaa ttgataagca ttgatgccaa atgcacttac taactgttct     660
atattgtagg aaaaatctaa cttttatatt aaaaatttat tttcataaaa cttccctaat     720
ttttgaacaa aatcttatat tgattttttt aatcaaagcc aaaatattta tttaactatg     780 aaaattttt  aacaactaat ttattatggt aaataatatt gatatggtaa ctttcagcac     840
atgacaaaaa ttataactaa ctgcagaagt ttactgtctc tctgaatctt gtggctatgt     900
cattctatca taacaaatac ttgtagctaa tacgccaacg atgttctcga tttcatataa     960
tttgaatttt aaaatagctt ttaaatttaa tatttatttc aaatcattat tgtgactaac    1020
atgttataac cgcagtaata tttggagatg caatacttat atttagctac aaaatttat    1080 tgtatcataa taagtttgta gctattaagt tagttttgc cacaaatttt tataattgaa     1140
```

| | |
|---|---|
| gcaaaaatac ctattcaact acaatatttt gtatcgagta atattttgtg actagaagat | 1200 |
| taatattatt acagtaattt ctgacgtgtg gcaaaaactc ataattatct acaaaatatt | 1260 |
| gtcgtagcaa taatttttta tatctattaa tccaattatt gctacatgct tttataactt | 1320 |
| gaggcaaaaa tatctatttta gctataacat tttgttagaa gtaattttg tgactataaa | 1380 |
| gttgttattg ctacagtaat ttcaaatgcg tggcaaaaaa aatacgatta gctacgaaat | 1440 |
| tttattgtag caataaattt gtagctattt gggtaatatt gctacgacag ttagcaatta | 1500 |
| tagcaaaaat gctaaatcag ctttgtcgat ttaattttgt agctaatttt tttatgaatt | 1560 |
| tgtaaatagc tatgaaattt taattttgt ggctattgtt aggtattagc cacatatagc | 1620 |
| taagaatttg tagctatata tacataatgt tgtagtggca aattctaaca ttgtaagctt | 1680 |
| ggctgccttt ttttttttt gggctacaaa actctaaagt aaaggaacta gaaaactcgt | 1740 |
| ttggcgagag aaagag | 1756 |

<210> SEQ ID NO 2
<211> LENGTH: 1851
<212> TYPE: DNA
<213> ORGANISM: Artificial Sequence
<220> FEATURE:
<223> OTHER INFORMATION: sythentic polynucleotide

<400> SEQUENCE: 2

| | |
|---|---|
| taagttgata aagctaattt ctcattttag ctaccatcgc tagtaatcgt ggcaataact | 60 |
| accctaacta tagcatttat tgctaccaaa taaaatttgg cagctaatca taatttttg | 120 |
| tcatgaatca atagttattg tagcaatagt tatctcttag ccacaataaa ttatttaaaa | 180 |
| taaaatatta tagctaaata aatattttg ctttaagttc taaaaggttg tggcaatagt | 240 |
| taaatgatat agtcacagat ttattggtat aattgaatta tgttgctaat ttcttagttt | 300 |
| tttgccacga gttaaaaatt accaatagct atagtaactt tttaatcaca ataaaatatt | 360 |
| tgaaagaaaa tattgtagct aaatgaatat ttttccttc aagttattaa aagttgtggc | 420 |
| aatataggtt aaattagcca catgtttctt gctttaatag aattttgtag ctaatcatta | 480 |
| acttttacca cgagttgaac ttaatataac aacaataacc ttttaaccat aataaagcga | 540 |
| tttaaatcaa atattactaa ataaataact ttgctttcaa gtttctataa aatcatggca | 600 |
| atagtcatta cgataaaatg atataaccac gaatatattg caacgataaa ttctgtaact | 660 |
| aatcattagt ttttgcgacg aggtaaattt tccgtcacag tagcaatctt ctaggcacat | 720 |
| taaaaatttg aaacaaaatt ttgtagtcaa ataaatattt atcttcttat tttaagaaaa | 780 |
| taaaaatagt tagataatag ttactactat ttgtcatgaa aatatcaata gatacaaatt | 840 |
| taaagtgact ataaatttac gagtttacta tactttagtc gtacagtttg caataatagt | 900 |
| attttaacca caattagtta tatgtacaaa ataacataag tgaataactt tttttcaatg | 960 |
| agaaaataag agttgctcaa acaatatcaa gttacaaaaa tttaattta actgtaaaag | 1020 |
| ttatatttt ccaaaataac ataaactata gtaattatat atagtttgaa gtattaataa | 1080 |
| aatttaaata tgcaaaagtt aattttaata aaccatttgt atgcctaact tgtagcctct | 1140 |
| aaactatttt atttgcttta tttatcaaac tcatattta ttttattgca ccttgttagt | 1200 |
| tttggacgtt aattatatat atttggtgta aaatttaaaa tatattaaca tttgtggaga | 1260 |
| atttatgtat gcctggttct taactatttt ttttatata actggttaga gtaatttctt | 1320 |
| atatttcagt atttatttt aaataagtcc tcataaattg aagactttaa aagtttttgt | 1380 |

```
gtcattcctc tttttattta agaaattgaa gaattccgct aaatttcata tttccgctgt   1440
tatttaactg tttatttccc ttgttaatat aattggtaag aagttttaaa ataaaggagt   1500
taatgatttt ctaggttcat ggcttgccta gcttctacga gtaagcgcca tcacgactcc   1560
cgaggataag gaaatcCggg tcgtagcatt cactcacaaa aattactaaa aacaaagttt   1620
acccttctcc caaaagtaaa tttcatattt ggctccacat aatgtgttca atgagtcaag   1680
tgaagtactt ttcatgacaa aaaaaagttg ctgaaaaatg catatctcat atttttttt    1740 tagagaaatc catttcttgc ctaaacgaaa gcctataaaa gagcatatat tgcaacaaca   1800
gtttgcagaa actatcaagt caaataatcc cccctttaat tccctcccaa a            1851
```

```
<210> SEQ ID NO 3
<211> LENGTH: 706
<212> TYPE: DNA
<213> ORGANISM: Artificial Sequence
<220> FEATURE:
<223> OTHER INFORMATION: synthetic polynucelotide

<400> SEQUENCE: 3
aatgacaaga agaaaatctt cgtcaacatg gtggagcacg acacgcttgt ctacctccaa     60
aaatatcaaa gatacagtct cagaagacca aagggaattg agacttttca acaagggta    120 atatccggaa acctcctcgg attccattgc ccagctatct gtcactttat tgtgaagata   180
gtggaaaagg aaggtggctc ctacaaatgc catcattgcg ataaaggaaa ggccatcgtt   240
gaagatgcct ctgccgacag tggtcccaaa gatggacccc cacccacgag gagcatcgtg   300 gaaaagaag acgttccaac cacgtcttca agcaagtgg attgatgtga taacatggtg    360
gagcacgaca cgcttgtcta cctccaaaaa tatcaaagat acagtctcag aagaccaaag   420
ggaattgaga ctttttcaaca aagggtaata tccggaaacc tcctcggatt ccattgccca   480
gctatctgtc actttattgt gaagatagtg gaaaggaag gtggctccta caaatgccat    540
cattgcgata aaggaaaggc catcgttgaa gatgcctctg ccgacagtgg tcccaaagat   600
ggacccccac ccacgaggag catcgtggaa aagaagacg ttccaaccac gtcttcaaag   660
caagtggatt gatgtgatat ctccactgac gtaagggatg acgcac                  706

<210> SEQ ID NO 4
<211> LENGTH: 1335
<212> TYPE: DNA
<213> ORGANISM: Saccharomyces cerevisiae

<400> SEQUENCE: 4
atgggaaagc tattacaatt ggcattgcat ccggtcgaga tgaaggcagc tttgaagctg    60
aagttttgca gaacaccgct attctccatc tatgatcagt ccacgtctcc atatctcttg   120
cactgtttcg aactgttgaa cttgacctcc agatcgtttg ctgctgtgat cagagagctg   180
catccagaat tgagaaactg tgttactctc ttttatttga ttttaaggc tttggatacc   240 atcgaagacg atatgtccat cgaacacgat ttgaaaattg acttgttgcg tcacttccac   300
gagaaattgt tgttaactaa atggagtttc gacggaaatg ccccgatgt gaaggacaga   360 gccgttttga cagatttcga atcgattctt attgaattcc acaaattgaa accagaatat   420
caagaagtca tcaaggagat caccgagaaa atgggtaatg gtatggccga ctacatctta   480
gatgaaaatt acaacttgaa tgggttgcaa accgtccacg actacgacgt gtactgtcac   540
tacgtagctg gtttggtcgg tgatggtttg accgtttga ttgtcattgc caagtttgcc    600
aacgaatctt tgtattctaa tgagcaattg tatgaaagca tgggtcttt cctacaaaaa   660
```

| | | | | |
|---|---|---|---|---|
| accaacatca | tcagagatta | caatgaagat | ttggtcgatg | gtagatcctt | ctggcccaag | 720 |
| gaaatctggt | cacaatacgc | tcctcagttg | aaggacttca | tgaaacctga | aaacgaacaa | 780 |
| ctggggttgg | actgtataaa | ccacctcgtc | ttaaacgcat | tgagtcatgt | tatcgatgtg | 840 |
| ttgacttatt | tggccggtat | ccacgagcaa | tccactttcc | aattttgtgc | cattccccaa | 900 |
| gttatggcca | ttgcaacctt | ggctttggta | ttcaacaacc | gtgaagtgct | acatggcaat | 960 |
| gtaaagattc | gtaagggtac | tacctgctat | ttaattttga | aatcaaggac | tttgcgtggc | 1020 |
| tgtgtcgaga | ttttgactga | ttacttacgt | gatatcaaat | ctaaattggc | tgtgcaagat | 1080 |
| ccaaatttct | taaaattgaa | cattcaaatc | tccaagatcg | aacagtttat | ggaagaaatg | 1140 |
| taccaggata | aattacctcc | taacgtgaag | ccaaatgaaa | ctccaatttt | cttgaaagtt | 1200 |
| aaagaaagat | ccagatacga | tgatgaattg | gttccaaccc | aacaagaaga | agagtacaag | 1260 |
| ttcaatatgg | ttttatctat | catcttgtcc | gttcttcttg | ggttttatta | tatatacact | 1320 |
| ttacacagag | cgtga | | | | | 1335 |

<210> SEQ ID NO 5
<211> LENGTH: 1137
<212> TYPE: DNA
<213> ORGANISM: unknown
<220> FEATURE:
<223> OTHER INFORMATION: avian

<400> SEQUENCE: 5

| | | | | |
|---|---|---|---|---|
| atgcagcccc | atcatcatca | taaagagggg | cgtatgcata | aatttactgg | tgtcaatgcc | 60 |
| aagtttcagc | aacccgcgtt | gaggaacctc | agcccgtgg | tggttgagag | ggagagggag | 120 |
| gagttcgtgg | ggttcttccc | gcagatcgtc | cgcgatctga | ccgaggacgg | catcggacac | 180 |
| ccggaggtgg | gcgacgctgt | ggcgcggctg | aaggaggtgc | tgcaatacaa | cgctcccggt | 240 |
| gggaaatgca | atcgtgggct | gacggtggtg | gctgcgtacc | gggagctgtc | ggggccgggg | 300 |
| cagaaggatg | ctgagagcct | gcggtgcgcg | ctggccgtgg | gttggtgcat | cgagttgttc | 360 |
| caggccttct | tcctggtggc | tgatgatatc | atggatcagt | ccctcacgcg | ccggggggcag | 420 |
| ctgtgttggt | ataagaagga | ggggtcggt | ttggatgcca | tcaacgactc | cttcctcctc | 480 |
| gagtcctctg | tgtacagagt | gctgaagaag | tactgcaggc | agcggccgta | ttacgtgcat | 540 |
| ctgttggagc | tcttcctgca | gaccgcctac | cagactgagc | tcgggcagat | gctggacctc | 600 |
| atcacagctc | ccgtctccaa | agtggatttg | agtcacttca | gcgaggagag | gtacaaagcc | 660 |
| atcgttaagt | acaagactgc | cttctactcc | ttctacctac | ccgtggctgc | tgccatgtat | 720 |
| atggttggga | tcgacagtaa | ggaagaacac | gagaatgcca | aagccatcct | gctggagatg | 780 |
| ggggaatact | tccagatcca | ggatgattac | ctggactgct | tggggaccc | ggcgctcacg | 840 |
| gggaaggtgg | gcaccgacat | ccaggacaat | aaatgcagct | ggctcgtggt | gcagtgcctg | 900 |
| cagcgcgtca | cgccggagca | gcggcagctc | tggaggaca | actacggccg | taaggagccc | 960 |
| gagaaggtgg | cgaaggtgaa | ggagctgtat | gaggccgtgg | ggatgagggc | tgcgttccag | 1020 |
| cagtacgagg | agagcagcta | ccggcgcctg | caggaactga | tagagaagca | ctcgaaccgc | 1080 |
| ctcccgaagg | agatcttcct | cggcctggca | cagaagatct | acaaacgcca | gaaatga | 1137 |

<210> SEQ ID NO 6
<211> LENGTH: 180
<212> TYPE: DNA
<213> ORGANISM: Artificial Sequence
<220> FEATURE:

<223> OTHER INFORMATION: synthetic polynucleotide

<400> SEQUENCE: 6

```
atggcttcct ctatgctctc ctccgccgct gtggttacat ccccggctca ggccaccatg    60
gtcgctccat tcaccggctt gaagtcatcc gctgcattcc cggtcacccg caagaccaac   120
aaggacatca cttccatcgc aagcaacggg ggaagatcta gctgcatgaa gactagtatg   180
```

<210> SEQ ID NO 7
<211> LENGTH: 342
<212> TYPE: PRT
<213> ORGANISM: Arabidopsis thaliana

<400> SEQUENCE: 7

```
Met Ala Asp Leu Lys Ser Thr Phe Leu Asp Val Tyr Ser Val Leu Lys
1               5                   10                  15

Ser Asp Leu Leu Gln Asp Pro Ser Phe Glu Phe Thr His Glu Ser Arg
            20                  25                  30

Gln Trp Leu Glu Arg Met Leu Asp Tyr Asn Val Arg Gly Gly Lys Leu
        35                  40                  45

Asn Arg Gly Leu Ser Val Val Asp Ser Tyr Lys Leu Leu Lys Gln Gly
    50                  55                  60

Gln Asp Leu Thr Glu Lys Glu Thr Phe Leu Ser Cys Ala Leu Gly Trp
65                  70                  75                  80

Cys Ile Glu Trp Leu Gln Ala Tyr Phe Leu Val Leu Asp Asp Ile Met
                85                  90                  95

Asp Asn Ser Val Thr Arg Arg Gly Gln Pro Cys Trp Phe Arg Lys Pro
            100                 105                 110

Lys Val Gly Met Ile Ala Ile Asn Asp Gly Ile Leu Leu Arg Asn His
        115                 120                 125

Ile His Arg Ile Leu Lys Lys His Phe Arg Glu Met Pro Tyr Tyr Val
    130                 135                 140

Asp Leu Val Asp Leu Phe Asn Glu Val Glu Phe Gln Thr Ala Cys Gly
145                 150                 155                 160

Gln Met Ile Asp Leu Ile Thr Thr Phe Asp Gly Glu Lys Asp Leu Ser
                165                 170                 175

Lys Tyr Ser Leu Gln Ile His Arg Arg Ile Val Glu Tyr Lys Thr Ala
            180                 185                 190

Tyr Tyr Ser Phe Tyr Leu Pro Val Ala Cys Ala Leu Leu Met Ala Gly
        195                 200                 205

Glu Asn Leu Glu Asn His Thr Asp Val Lys Thr Val Leu Val Asp Met
    210                 215                 220

Gly Ile Tyr Phe Gln Val Gln Asp Asp Tyr Leu Asp Cys Phe Ala Asp
225                 230                 235                 240

Pro Glu Thr Leu Gly Lys Ile Gly Thr Asp Ile Glu Asp Phe Lys Cys
                245                 250                 255

Ser Trp Leu Val Val Lys Ala Leu Glu Arg Cys Ser Glu Glu Gln Thr
            260                 265                 270

Lys Ile Leu Tyr Glu Asn Tyr Gly Lys Ala Glu Pro Ser Asn Val Ala
        275                 280                 285

Lys Val Lys Ala Leu Tyr Lys Glu Leu Asp Leu Glu Gly Ala Phe Met
    290                 295                 300

Glu Tyr Glu Lys Glu Ser Tyr Glu Lys Leu Thr Lys Leu Ile Glu Ala
305                 310                 315                 320

His Gln Ser Lys Ala Ile Gln Ala Val Leu Lys Ser Phe Leu Ala Lys
```

325                 330                 335

Ile Tyr Lys Arg Gln Lys
            340

<210> SEQ ID NO 8
<211> LENGTH: 1266
<212> TYPE: DNA
<213> ORGANISM: Arabidopsis thaliana

<400> SEQUENCE: 8
aatcaggttc cacatttggc tttgcacacc ttccttgatc ctatcaatgg cggatctgaa      60
atcaaccttc ctcgacgttt actctgttct caagtctgat ctgcttcaag atccttcctt     120
tgaattcacc cacgaatctc gtcaatggct tgaacggatg cttgactaca atgtacgcgg     180
agggaagcta atcgtggtc tctctgtggt tgatagctac aagctgttga agcaaggtca      240
agacttgacg gagaaagaga ctttcctctc atgtgctctt ggttggtgca ttgaatggct     300
tcaagcttat ttccttgtgc ttgatgacat catggacaac tctgtcacac gccgtggcca     360
gccttgttgg tttagaaagc caaggttgg tatgattgcc attaacgatg ggattctact      420
tcgcaatcat atccacagga ttctcaaaaa gcacttcagg gaaatgcctt actatgttga     480
cctcgttgat ttgtttaacg aggtagagtt tcaaacagct gcggccaga tgattgattt      540
gatcaccacc tttgatggag aaaaagattt gtctaagtac tccttgcaaa tccatcggcg     600
tattgttgag tacaaaacag cttattactc attttatctt cctgttgctt gcgcattgct     660
catggcggga aaaatttgg aaaaccatac tgatgtgaag actgttcttg ttgacatggg      720
aatttacttt caagtacagg atgattatct ggactgtttt gctgatcctg agacacttgg     780
caagatagg acagacatag aagatttcaa atgctcctgg ttggtagtta aggcattgga      840
acgctgcagt gaagaacaaa ctaagatact atacgagaac tatggtaaag ccgaaccatc     900
aaacgttgct aaggtgaaag ctctctacaa agagcttgat ctcgagggag cgttcatgga     960
atatgagaag gaaagctatg agaagctgac aaagttgatc gaagctcacc agagtaaagc    1020
aattcaagca gtgctaaaat ctttcttggc taagatctac aagaggcaga agtagagaca    1080
tactcgggcc tctctccgtt ttattcttct gacatttatg tattggtgca tgacttcttt    1140
tgccttagat cttatgttcc cttccgaaaa tagaatttga gattcttgtt catgcttata    1200
gtatagagac ttagaaaatg tctatgtttc ttttaatttc tgaataaaaa atgtgcaatc    1260
agtgat                                                              1266

<210> SEQ ID NO 9
<211> LENGTH: 384
<212> TYPE: PRT
<213> ORGANISM: Arabidopsis thaliana

<400> SEQUENCE: 9

Met Ser Val Ser Cys Cys Cys Arg Asn Leu Gly Lys Thr Ile Lys Lys
 1               5                  10                  15

Ala Ile Pro Ser His His Leu His Leu Arg Ser Leu Gly Gly Ser Leu
                20                  25                  30

Tyr Arg Arg Arg Ile Gln Ser Ser Met Glu Thr Asp Leu Lys Ser
            35                  40                  45

Thr Phe Leu Asn Val Tyr Ser Val Leu Lys Ser Asp Leu Leu His Asp
    50                  55                  60

Pro Ser Phe Glu Phe Thr Asn Glu Ser Arg Leu Trp Val Asp Arg Met
65                  70                  75                  80

```
Leu Asp Tyr Asn Val Arg Gly Lys Leu Asn Arg Gly Leu Ser Val
                 85                  90                  95

Val Asp Ser Phe Lys Leu Leu Lys Gln Gly Asn Asp Leu Thr Glu Gln
            100                 105                 110

Glu Val Phe Leu Ser Cys Ala Leu Gly Trp Cys Ile Glu Trp Leu Gln
        115                 120                 125

Ala Tyr Phe Leu Val Leu Asp Asp Ile Met Asp Asn Ser Val Thr Arg
    130                 135                 140

Arg Gly Gln Pro Cys Trp Phe Arg Val Pro Gln Val Gly Met Val Ala
145                 150                 155                 160

Ile Asn Asp Gly Ile Leu Leu Arg Asn His Ile His Arg Ile Leu Lys
                165                 170                 175

Lys His Phe Arg Asp Lys Pro Tyr Tyr Val Asp Leu Val Asp Leu Phe
            180                 185                 190

Asn Glu Val Glu Leu Gln Thr Ala Cys Gly Gln Met Ile Asp Leu Ile
        195                 200                 205

Thr Thr Phe Glu Gly Glu Lys Asp Leu Ala Lys Tyr Ser Leu Ser Ile
    210                 215                 220

His Arg Arg Ile Val Gln Tyr Lys Thr Ala Tyr Tyr Ser Phe Tyr Leu
225                 230                 235                 240

Pro Val Ala Cys Ala Leu Leu Met Ala Gly Glu Asn Leu Glu Asn His
                245                 250                 255

Ile Asp Val Lys Asn Val Leu Val Asp Met Gly Ile Tyr Phe Gln Val
            260                 265                 270

Gln Asp Asp Tyr Leu Asp Cys Phe Ala Asp Pro Glu Thr Leu Gly Lys
        275                 280                 285

Ile Gly Thr Asp Ile Glu Asp Phe Lys Cys Ser Trp Leu Val Val Lys
    290                 295                 300

Ala Leu Glu Arg Cys Ser Glu Glu Gln Thr Lys Ile Leu Tyr Glu Asn
305                 310                 315                 320

Tyr Gly Lys Pro Asp Pro Ser Asn Val Ala Lys Val Lys Asp Leu Tyr
                325                 330                 335

Lys Glu Leu Asp Leu Glu Gly Val Phe Met Glu Tyr Glu Ser Lys Ser
            340                 345                 350

Tyr Glu Lys Leu Thr Gly Ala Ile Glu Gly His Gln Ser Lys Ala Ile
        355                 360                 365

Gln Ala Val Leu Lys Ser Phe Leu Ala Lys Ile Tyr Lys Arg Gln Lys
    370                 375                 380

<210> SEQ ID NO 10
<211> LENGTH: 1155
<212> TYPE: DNA
<213> ORGANISM: Arabidopsis thaliana

<400> SEQUENCE: 10
atgagtgtga gttgttgttg taggaatctg ggcaagacaa taaaaaggc aataccttca      60 catcatttgc atctgagaag tcttggtggg agtctctatc gtcgtcgtat ccaaagctct    120
tcaatggaga ccgatctcaa gtcaaccttt ctcaacgttt attctgttct caagtctgac    180
cttcttcatg acccttcctt cgaattcacc aatgaatctc gtctctgggt tgatcggatg    240
ctggactaca atgtacgtgg agggaaactc aatcggggtc tctctgttgt tgacagtttc    300 aaactttga agcaaggcaa tgatttgact gagcaagagg ttttcctctc ttgtgctctc    360
ggttggtgca ttgaatggct ccaagcttat ttccttgtgc ttgatgatat tatggataac    420
```

```
tctgtcactc gccgtggtca accttgctgg ttcagagttc ctcaggttgg tatggttgcc    480
atcaatgatg ggattctact tcgcaatcac atccacagga ttctcaaaaa gcatttccgt    540
gataagcctt actatgttga ccttgttgat ttgtttaatg aggttgagtt gcaaacagct    600
tgtggccaga tgatagattt gatcaccacc tttgaaggag aaaaggattt ggccaagtac    660
tcattgtcaa tccaccgtcg tattgtccag tacaaaacgg cttattactc attttatctc    720
cctgttgctt gtgcgttgct tatggcgggc gaaaatttgg aaaaccatat tgacgtgaaa    780
aatgttcttg ttgacatggg aatctacttc caagtgcagg atgattatct ggattgtttt    840
gctgatcccg agacgcttgg caagatagga acagatatag aagatttcaa atgctcgtgg    900
ttggtggtta aggcattaga gcgctgcagc gaagaacaaa ctaagatatt atatgagaac    960
tatggtaaac ccgacccatc gaacgttgct aaagtgaagg atctctacaa agagctggat   1020
cttgagggag ttttcatgga gtatgagagc aaaagctacg agaagctgac tggagcgatt   1080
gagggacacc aaagtaaagc aatccaagca gtgctaaaat ccttcttggc taagatctac   1140
aagaggcaga agtag                                                    1155

<210> SEQ ID NO 11
<211> LENGTH: 352
<212> TYPE: PRT
<213> ORGANISM: Saccharomyces cerevisiae

<400> SEQUENCE: 11

Met Ala Ser Glu Lys Glu Ile Arg Arg Glu Arg Phe Leu Asn Val Phe
1               5                   10                  15

Pro Lys Leu Val Glu Glu Leu Asn Ala Ser Leu Leu Ala Tyr Gly Met
            20                  25                  30

Pro Lys Glu Ala Cys Asp Trp Tyr Ala His Ser Leu Asn Tyr Asn Thr
        35                  40                  45

Pro Gly Gly Lys Leu Asn Arg Gly Leu Ser Val Val Asp Thr Tyr Ala
    50                  55                  60

Ile Leu Ser Asn Lys Thr Val Glu Gln Leu Gly Gln Glu Glu Tyr Glu
65                  70                  75                  80

Lys Val Ala Ile Leu Gly Trp Cys Ile Glu Leu Leu Gln Ala Tyr Phe
                85                  90                  95

Leu Val Ala Asp Asp Met Met Asp Lys Ser Ile Thr Arg Arg Gly Gln
            100                 105                 110

Pro Cys Trp Tyr Lys Val Pro Glu Val Gly Glu Ile Ala Ile Asn Asp
        115                 120                 125

Ala Phe Met Leu Glu Ala Ala Ile Tyr Lys Leu Leu Lys Ser His Phe
    130                 135                 140

Arg Asn Glu Lys Tyr Tyr Ile Asp Ile Thr Glu Leu Phe His Glu Val
145                 150                 155                 160

Thr Phe Gln Thr Glu Leu Gly Gln Leu Met Asp Leu Ile Thr Ala Pro
                165                 170                 175

Glu Asp Lys Val Asp Leu Ser Lys Phe Ser Leu Lys Lys His Ser Phe
            180                 185                 190

Ile Val Thr Phe Lys Thr Ala Tyr Tyr Ser Phe Tyr Leu Pro Val Ala
        195                 200                 205

Leu Ala Met Tyr Val Ala Gly Ile Thr Asp Glu Lys Asp Leu Lys Gln
    210                 215                 220

Ala Arg Asp Val Leu Ile Pro Leu Gly Glu Tyr Phe Gln Ile Gln Asp
225                 230                 235                 240
```

Asp Tyr Leu Asp Cys Phe Gly Thr Pro Glu Gln Ile Gly Lys Ile Gly
            245                 250                 255

Thr Asp Ile Gln Asp Asn Lys Cys Ser Trp Val Ile Asn Lys Ala Leu
        260                 265                 270

Glu Leu Ala Ser Ala Glu Gln Arg Lys Thr Leu Asp Glu Asn Tyr Gly
    275                 280                 285

Lys Lys Asp Ser Val Ala Glu Ala Lys Cys Lys Lys Ile Phe Asn Asp
290                 295                 300

Leu Lys Ile Glu Gln Leu Tyr His Glu Tyr Glu Ser Ile Ala Lys
305                 310                 315                 320

Asp Leu Lys Ala Lys Ile Ser Gln Val Asp Glu Ser Arg Gly Phe Lys
                325                 330                 335

Ala Asp Val Leu Thr Ala Phe Leu Asn Lys Val Tyr Lys Arg Ser Lys
            340                 345                 350

<210> SEQ ID NO 12
<211> LENGTH: 1059
<212> TYPE: DNA
<213> ORGANISM: Saccharomyces cerevisiae

<400> SEQUENCE: 12
atggcttcag aaaagaaat taggagagag agattcttga acgttttccc taaattagta      60
gaggaattga acgcatcgct tttggcttac ggtatgccta aggaagcatg tgactggtat     120
gcccactcat tgaactacaa cactccaggc ggtaagctaa atagaggttt gtccgttgtg     180
gacacgtatg ctattctctc caacaagacc gttgaacaat ggggcaaga agaatacgaa      240
aaggttgcca ttctaggttg gtgcattgag ttgttgcagg cttacttctt ggtcgccgat     300
gatatgatgg acaagtccat taccagaaga ggccaaccat gttggtacaa ggttcctgaa     360
gttggggaaa ttgccatcaa tgacgcattc atgttagagg ctgctatcta caagcttttg     420
aaatctcact tcagaaacga aaatactac atagatatca ccgaattgtt ccatgaggtc      480
accttccaaa ccgaattggg ccaattgatg gacttaatca ctgcacctga gacaaagtc      540
gacttgagta agttctccct aaagaagcac tccttcatag ttactttcaa gactgcttac     600
tattctttct acttgcctgt cgcattggcc atgtacgttg ccggtatcac ggatgaaaag     660
gatttgaaac aagccagaga tgtcttgatt ccattgggtg aatacttcca aattcaagat     720
gactacttag actgcttcgg taccccagaa cagatcggta agatcggtac agatatccaa     780
gataacaaat gttcttgggt aatcaacaag gcattggaac ttgcttccgc agaacaaaga     840
aagactttag acgaaaatta cggtaagaag gactcagtcg cagaagccaa atgcaaaaag     900
attttcaatg acttgaaaat tgaacagcta taccacgaat atgaagagtc tattgccaag     960
gatttgaagg ccaaaatttc tcaggtcgat gagtctcgtg gcttcaaagc tgatgtctta    1020
actgcgttct tgaacaaagt ttacaagaga agcaaatag                           1059

<210> SEQ ID NO 13
<211> LENGTH: 419
<212> TYPE: PRT
<213> ORGANISM: Homo sapiens

<400> SEQUENCE: 13

Met Pro Leu Ser Arg Trp Leu Arg Ser Val Gly Val Phe Leu Leu Pro
1               5                   10                  15

Ala Pro Tyr Trp Ala Pro Arg Glu Arg Trp Leu Gly Ser Leu Arg Arg
            20                  25                  30

Pro Ser Leu Val His Gly Tyr Pro Val Leu Ala Trp His Ser Ala Arg
        35                  40                  45

Cys Trp Cys Gln Ala Trp Thr Glu Glu Pro Arg Ala Leu Cys Ser Ser
    50                  55                  60

Leu Arg Met Asn Gly Asp Gln Asn Ser Asp Val Tyr Ala Gln Glu Lys
65                  70                  75                  80

Gln Asp Phe Val Gln His Phe Ser Gln Ile Val Arg Val Leu Thr Glu
                85                  90                  95

Asp Glu Met Gly His Pro Glu Ile Gly Asp Ala Ile Ala Arg Leu Lys
            100                 105                 110

Glu Val Leu Glu Tyr Asn Ala Ile Gly Gly Lys Tyr Asn Arg Gly Leu
        115                 120                 125

Thr Val Val Ala Phe Arg Glu Leu Val Glu Pro Arg Lys Gln Asp
130                 135                 140

Ala Asp Ser Leu Gln Arg Ala Trp Thr Val Gly Trp Cys Val Glu Leu
145                 150                 155                 160

Leu Gln Ala Phe Phe Leu Val Ala Asp Asp Ile Met Asp Ser Ser Leu
                165                 170                 175

Thr Arg Arg Gly Gln Ile Cys Trp Tyr Gln Lys Pro Gly Val Gly Leu
            180                 185                 190

Asp Ala Ile Asn Asp Ala Asn Leu Leu Glu Ala Cys Ile Tyr Arg Leu
        195                 200                 205

Leu Lys Leu Tyr Cys Arg Glu Gln Pro Tyr Tyr Leu Asn Leu Ile Glu
    210                 215                 220

Leu Phe Leu Gln Ser Ser Tyr Gln Thr Glu Ile Gly Gln Thr Leu Asp
225                 230                 235                 240

Leu Leu Thr Ala Pro Gln Gly Asn Val Asp Leu Val Arg Phe Thr Glu
                245                 250                 255

Lys Arg Tyr Lys Ser Ile Val Lys Tyr Lys Thr Ala Phe Tyr Ser Phe
            260                 265                 270

Tyr Leu Pro Ile Ala Ala Ala Met Tyr Met Ala Gly Ile Asp Gly Glu
        275                 280                 285

Lys Glu His Ala Asn Ala Lys Lys Ile Leu Leu Glu Met Gly Glu Phe
    290                 295                 300

Phe Gln Ile Gln Asp Asp Tyr Leu Asp Leu Phe Gly Asp Pro Ser Val
305                 310                 315                 320

Thr Gly Lys Ile Gly Thr Asp Ile Gln Asp Asn Lys Cys Ser Trp Leu
                325                 330                 335

Val Val Gln Cys Leu Gln Arg Ala Thr Pro Glu Gln Tyr Gln Ile Leu
            340                 345                 350

Lys Glu Asn Tyr Gly Gln Lys Glu Ala Glu Lys Val Ala Arg Val Lys
        355                 360                 365

Ala Leu Tyr Glu Glu Leu Asp Leu Pro Ala Val Phe Leu Gln Tyr Glu
370                 375                 380

Glu Asp Ser Tyr Ser His Ile Met Ala Leu Ile Glu Gln Tyr Ala Ala
385                 390                 395                 400

Pro Leu Pro Pro Ala Val Phe Leu Gly Leu Ala Arg Lys Ile Tyr Lys
                405                 410                 415

Arg Arg Lys

<210> SEQ ID NO 14
<211> LENGTH: 1260
<212> TYPE: DNA

<213> ORGANISM: Homo sapiens

<400> SEQUENCE: 14

```
atgcccctgt cccgctggtt gagatctgtg ggggtcttcc tgctgccagc cccctactgg    60
gcacccgggg agaggtggct gggttcccta cggcggccct ccctggtgca cgggtaccca   120
gtcctggcct ggcacagtgc ccgctgctgg tgccaagcgt ggacagagga acctcgagcc   180
ctttgctcct ccctcagaat gaacggagac cagaattcag atgtttatgc caagaaaaag   240
caggatttcg ttcagcactt ctcccagatc gttagggtgc tgactgagga tgagatgggg   300
cacccagaga taggagatgc tattgcccgg ctcaaggagg tcctggagta caatgccatt   360
ggaggcaagt ataaccgggg tttgacggtg gtagtagcat ccgggagct ggtggagcca   420
aggaaacagg atgctgatag tctccagcgg gcctggactg tgggctggtg tgtggaactg   480
ctgcaagctt tcttcctggt ggcagatgac atcatggatt catcccttac ccgccgggga   540
cagatctgct ggtatcagaa gccgggcgtg ggtttggatg ccatcaatga tgctaacctc   600
ctggaagcat gtatctaccg cctgctgaag ctctattgcc gggagcagcc ctattacctg   660
aacctgatcg agctcttcct gcagagttcc tatcagactg agattgggca gaccctggac   720
ctcctcacag ccccccaggg caatgtggat cttgtcagat tcactgaaaa gaggtacaaa   780
tctattgtca agtacaagac agctttctac tccttctacc ttcctatagc tgcagccatg   840
tacatggcag gaattgatgg cgagaaggag cacgccaatg ccaagaagat cctgctggag   900
atgggggagt tctttcagat tcaggatgat taccttgacc tctttgggga ccccagtgtg   960
accggcaaaa ttggcactga catccaggac aacaaatgca gctggctggt ggttcagtgt  1020
ctgcaacggg ccactccaga acagtaccag atcctgaagg aaaattacgg cagaaggag   1080
gctgagaaag tggcccgggt gaaggcgcta tatgaggagc tggatctgcc agcagtgttc  1140
ttgcaatatg aggaagacag ttacagccac attatggctc tcattgaaca gtacgcagca  1200
ccctgccc cagccgtctt tctggggctt gcgcgcaaaa tctacaagcg gagaaagtga   1260
```

<210> SEQ ID NO 15
<211> LENGTH: 360
<212> TYPE: PRT
<213> ORGANISM: Chlamydomonas reinhardtii

<400> SEQUENCE: 15

```
Met Ser Gly Glu Pro Thr Pro Lys Lys Met Lys Ala Thr Tyr Val His
1               5                   10                  15

Asp Arg Glu Asn Phe Thr Lys Val Tyr Glu Thr Leu Arg Asp Glu Leu
            20                  25                  30

Leu Asn Asp Asp Cys Leu Ser Pro Ala Gly Ser Pro Gln Ala Gln Ala
        35                  40                  45

Ala Gln Glu Trp Phe Lys Glu Val Asn Asp Tyr Asn Val Pro Gly Gly
    50                  55                  60

Lys Leu Asn Arg Gly Met Ala Val Tyr Asp Val Leu Ala Ser Val Lys
65                  70                  75                  80

Gly Pro Asp Gly Leu Ser Glu Asp Glu Val Phe Lys Ala Asn Ala Leu
                85                  90                  95

Gly Trp Cys Ile Glu Trp Leu Gln Ala Phe Phe Leu Val Ala Asp Asp
            100                 105                 110

Ile Met Asp Gly Ser Ile Thr Arg Arg Gly Gln Pro Cys Trp Tyr Lys
        115                 120                 125

Gln Pro Lys Val Gly Met Ile Ala Cys Asn Asp Tyr Ile Leu Leu Glu
```

```
                    130              135               140
Cys Cys Ile Tyr Ser Ile Leu Lys Arg His Phe Arg Gly His Ala Ala
145                 150               155                 160

Tyr Ala Gln Leu Met Asp Leu Phe His Glu Thr Thr Phe Gln Thr Ser
                    165               170                 175

His Gly Gln Leu Leu Asp Leu Thr Thr Ala Pro Ile Gly Ser Val Asp
                180                   185                 190

Leu Ser Lys Tyr Thr Glu Asp Asn Tyr Leu Arg Ile Val Thr Tyr Lys
            195                   200                 205

Thr Ala Tyr Tyr Ser Phe Tyr Leu Pro Val Ala Cys Gly Met Val Leu
        210                   215                 220

Ala Gly Ile Thr Asp Pro Ala Ala Phe Asp Leu Ala Lys Asn Ile Cys
225                 230                   235                 240

Val Glu Met Gly Gln Tyr Phe Gln Ile Gln Asp Tyr Leu Asp Cys
                    245                   250                 255

Tyr Gly Asp Pro Glu Val Ile Gly Lys Ile Gly Thr Asp Ile Glu Asp
                260                   265                 270

Asn Lys Cys Ser Trp Leu Val Cys Thr Ala Leu Lys Ile Ala Thr Glu
            275                   280                 285

Glu Gln Lys Glu Val Ile Lys Ala Asn Tyr Gly His Lys Glu Ala Glu
        290                   295                 300

Ser Val Ala Ala Ile Lys Ala Leu Tyr Val Glu Leu Gly Ile Glu Gln
305                 310                   315                 320

Arg Phe Lys Asp Tyr Glu Ala Ala Ser Tyr Ala Lys Leu Glu Gly Thr
                    325                   330                 335

Ile Ser Glu Gln Thr Leu Leu Pro Lys Ala Val Phe Thr Ser Leu Leu
                340                   345                 350

Ala Lys Ile Tyr Lys Arg Lys Lys
            355                   360

<210> SEQ ID NO 16
<211> LENGTH: 1083
<212> TYPE: DNA
<213> ORGANISM: Chlamydomonas reinhardtii

<400> SEQUENCE: 16
atgagcggcg agcctacccc caaaaagatg aaggccactt acgtgcacga ccgcgagaac    60
tttacaaaag tatatgagac cctccgcgat gagctcctga cgacgactg cctgtcaccc    120 gccggcagtc ctcaggctca ggccgcgcag gagtggttca aggaggtgaa cgactacaac    180
gtgccgggcg gcaagctgaa ccgcggaatg gcggtatacg acgtgctggc atccgtgaag    240
gggcccgacg tctatccga ggatgaggtg ttcaaggcca acgcactggg ctggtgcatc    300
gagtggctgc aagcgttctt cctggtggcg acgacatca tggacggatc catcacccgc    360
cgcggccagc cctgctggta caagcagccc aaggtgggca tgatcgcctg caatgactac    420
atcctgctgg agtgctgcat ctactccatc ctcaagcgcc acttccgcgg ccacgccgcc    480
tatgcgcagc tgatggacct gttccacgag accacgttcc agaccagcca cggccagctg    540
ctggacctga ccactgctcc catcggctcc gtggacttgt ccaagtacac cgaggacaac    600
tacctgcgca ttgtgaccta caagaccgcc tactactcct ctacctgcc cgtggcgtgc    660 ggcatggttc tggcgggcat cacggacccg gccgccttcg acctggccaa gaacatttgt    720
gtggagatgg gccagtactt tcagatccag gatgactacc tagactgcta cggcgacccc    780
gaggtgattg gcaagattgg tacggacatc gaggacaaca gtgcagctg ctggtgtgc    840
```

| | |
|---|---|
| acggcgctga agattgccac cgaggagcag aaggaggtca tcaaggccaa ctacgggcac | 900 |
| aaggaggctg agtcggtggc cgccatcaag gcgctgtacg tggagctggg cattgagcag | 960 |
| cgcttcaagg actacgaggc cgcttcctac gccaagctgg agggcaccat ctcggagcag | 1020 |
| acgctgctgc ccaaggcggt gttcacgtcg ctactggcca agatctacaa gcgcaagaag | 1080 |
| taa | 1083 |

<210> SEQ ID NO 17
<211> LENGTH: 1263
<212> TYPE: DNA
<213> ORGANISM: Saccharomyces cerevisiae

<400> SEQUENCE: 17

| | |
|---|---|
| atgggaaagc tattacaatt ggcattgcat ccggtcgaga tgaaggcagc tttgaagctg | 60 |
| aagttttgca gaacaccgct attctccatc tatgatcagt ccacgtctcc atatctcttg | 120 |
| cactgtttcg aactgttgaa cttcacctcc agatcgtttg ctgctgtgat cagagagctg | 180 |
| catccagaat tgagaaactg tgttactctc ttttatttga ttttaagggc tttggatacc | 240 |
| atcgaagacg atatgtccat cgaacacgat ttgaaaattg acttgttgcg tcacttccac | 300 |
| gagaaattgt tgttaactaa atggagtttc gacggaaatg cccccgatgt gaaggacaga | 360 |
| gccgttttga cagatttcga atcgattctt attgaattcc acaaattgaa accagaatat | 420 |
| caagaagtca tcaaggagat caccgagaaa atgggtaatg gtatggccga ctacatctta | 480 |
| gatgaaaatt acaacttgaa tggggttgcaa accgtccacg actacgacgt gtactgtcac | 540 |
| tacgtagctg gtttggtcgg tgatggtttg acccgtttga ttgtcattgc caagtttgcc | 600 |
| aacgaatctt tgtattctaa tgagcaattg tatgaaagca tgggtctttt cctacaaaaa | 660 |
| accaacatca tcagagatta caatgaagat ttggtcgatg gtagatcctt ctggcccaag | 720 |
| gaaatctggt cacaatacgc tcctcagttg aaggacttca tgaaacctga aaacgaacaa | 780 |
| ctggggttgg actgtataaa ccacctcgtc ttaaacgcat tgagtcatgt tatcgatgtg | 840 |
| ttgacttatt tggccggtat ccacgagcaa tccactttcc aattttgtgc cattccccaa | 900 |
| gttatggcca ttgcaacctt ggctttggta ttcaacaacc gtgaagtgct acatggcgat | 960 |
| gtaaagattc gtaagggtac tacctgctgt ttaattttga aatcaaggac tttgcgtggc | 1020 |
| tgtgtcgaga ttttttgacta ttacttacgt gatatcaaat ctaaattggc tgtgcaagat | 1080 |
| ccaaatttct taaaattgaa cattcaaatc tccaagatcg aacagtttat ggaagaaatg | 1140 |
| taccaggata aattacctcc taacgtgaag ccaaatgaaa ctccaatttt cttgaaagtt | 1200 |
| aaagaaagat ccagatacga tgatgaattg gttccaaccc aacaagaaga agagtacaag | 1260 |
| tga | 1263 |

<210> SEQ ID NO 18
<211> LENGTH: 1059
<212> TYPE: DNA
<213> ORGANISM: Chlamydomonas reinhardtii

<400> SEQUENCE: 18

| | |
|---|---|
| atggggatgc ttcgctgggg agtggagtct ttgcagaatc cagatgaatt aatcccggtc | 60 |
| ttgaggatga tttatgctga taagtttgga aagatcaagc caaggacga agaccggggc | 120 |
| ttctgctatg aaattttaaa ccttgtttca agaagttttg caatcgtcat ccaacagctc | 180 |
| cctgcacagc tgagggaccc agtctgcata ttttaccttg tactacgcgc cctggacaca | 240 |

```
gtcgaagatg atatgaaaat tgcagcaacc accaagattc ccttgctgcg tgacttttat      300
gagaaaattt ctgacaggtc attccgcatg acggccggag atcaaaaaga ctacatcagg      360
ctgttggatc agtaccccaa agtgacaagc gttttcttga aattgacccc ccgtgaacaa      420
gagataattg cagacattac aaagcggatg gggaatggaa tggctgactt cgtgcataag      480
ggtgttcccg acacagtggg ggactacgac ctttactgcc actatgttgc tggggtggtg      540
ggtctcgggc tttcccagtt gttcgttgcg agtggactac agtcaccctc tttgacccgc      600
agtgaagacc tttccaatca catgggcctc ttccttcaga agaccaacat catccgcgac      660
tactttgagg acatcaatga gctgcctgcc ccccggatgt tctggcccag agagatctgg      720
ggcaagtatg cgaacaacct cgctgagttc aaagacccgg ccaacaaggc ggctgcaatg      780
tgctgcctca acgagatggt cacagatgca ttgaggcacg cggtgtactg cctgcagtac      840
atgtccatga ttgaggatcc gcagatcttc aacttctgtg ccatccctca gaccatggcc      900
ttcggcaccc tgtctttgtg ttacaacaac tacactatct tcacagggcc caaagcggct      960
gtgaagctgc gtaggggcac cactgccaag ctgatgtaca cctctaacaa tatgtttgcg     1020
atgtaccgtc atttcctcaa cttcgcagag aagctttga                            1059

<210> SEQ ID NO 19
<211> LENGTH: 1035
<212> TYPE: DNA
<213> ORGANISM: Arabidopsis thaliana

<400> SEQUENCE: 19
atggggagct tggggacgat gctgagatat ccggatgaca tatatccgct cctgaagatg       60
aaacgagcga ttgagaaagc ggagaagcag atccctcctg agccacactg gggtttctgc      120
tattcgatgc tccacaaggt ttctcgaagc ttttctctcg ttattcagca actcaacacc      180
gagctccgta acgccgtgtg tgtgttctac ttggttctcc gagctcttga tactgttgag      240
gatgatacta gcataccaac tgatgaaaag gttcccatcc tgatagcttt tcaccggcac      300
atatacgata ctgattggca ttattcatgt ggtacgaagg agtacaagat tctaatggac      360
caatttcacc atgtttctgc agcttttttg gaacttgaaa aagggtatca agaggctatc      420
gaggaaatta ctagaagaat gggtgcaggg atggccaagt ttatctgcca agaggtagaa      480
actgttgatg actacgatga atactgccac tatgttgctg gcttgttgg tttaggtttg      540 tcgaaactct tcctcgctgc aggatcagag gttttgacac cagattggga ggcgatttcc      600
aattcaatgg gtttatttct gcagaaaaca aacattatca gagattatct tgaggacatt      660
aatgagatac caaaatcccg catgttttgg cctcgcgaga tttggggcaa atatgctgac      720
aagcttgagg atttaaaata cgaggagaac acaaacaaat ccgtacagtg cttaaatgaa      780
atggttacca atgcgttgat gcatattgaa gattgcctga atacatggt ttccttgcgt      840 gatccttcca tatttcggtt ctgtgccatc cctcagatca tggcgattgg aacacttgca      900
ttatgctata caatgaaca agtattcaga ggcgttgtga aactgaggcg aggtcttact      960
gctaaagtca ttgatcgtac aaagacaatg gctgatgtct atggtgcttt ctatgatttt     1020
tcctgcatgc tgtga                                                       1035

<210> SEQ ID NO 20
<211> LENGTH: 1029
<212> TYPE: DNA
<213> ORGANISM: Nicotiana tabacum

<400> SEQUENCE: 20
```

```
atgggagtt tgagggctat tctgaagaat ccagaggatt tatatccatt ggtgaagctg     60
aagctagcgg ctcgacacgc ggagaagcag atcccgccgt ctccaaattg gggcttctgt   120
tactcaatgc ttcataaggt ttctcgtagc tttgctctcg tcattcaaca acttccagtc   180
gagcttcgtg acgccgtgtg cattttctat ttggttcttc gagcacttga cactgttgag   240
gatgatacca gcattcccac cgatgttaaa gttcctattc tgatctcttt tcatcagcat   300
gtttatgatc gcgaatggca ttttcatgt ggtacaaagg agtacaaggt tctcatggac    360
cagttccatc atgtatcaac tgcttttctg agcttagga acattatca gcaggcaatt     420 gaggatatta ccatgaggat gggtgcagga atggcaaaat tcatatgcaa ggaggtggaa   480
acaaccgatg attatgacga atattgtcac tatgtagctg ggcttgttgg gctaggattg   540
tcaaaactgt tccatgcctc tgagaaagaa gatctggctt cagattctct ctccaactcc   600
atgggtttat tcttcagaa aacaaacatc attagagatt atttggaaga cataaatgaa    660
gtacccaagt gccgtatgtt ctggccccgt gaaatatgga gtaaatatgt taacaagctt   720
gaggaattaa agtacgagga taactcggcc aaagcagtgc aatgtctaaa tgacatggtc   780
actaatgctt tatcacatgt agaagattgt ttgacttaca tgtctgcttt gcgtgatcct   840
tccatctttc gattctgtgc tattccacag gtcatggcaa ttgggacatt agctatgtgc   900
tacgacaaca ttgaagtctt cagaggagtg gtaaaaatga cgtggtct gactgctaag     960 gtcattgacc ggaccaggac tattgcagat gtatatggtg cttttttga cttttcttgt   1020 atgctgtga                                                          1029
```

<210> SEQ ID NO 21
<211> LENGTH: 1113
<212> TYPE: DNA
<213> ORGANISM: Rattus

<400> SEQUENCE: 21

```
atggagttcg tgaagtgtct aggccacccg gaggagttct acaacctgct gcgattccgc    60
atgggaggcc ggcggaattt catacccaag atggaccgga actgctcag caacagcttg    120 aagacttgct ataagtatct tgatcagacc agtcgcagct tcgccgcggt tatccaggcg   180
ctggatgggg acatacgtca tgcggtgtgt gtgttttacc tgatcctccg agccatggac   240
acagtggagg atgacatggc catcagtgtg agaagaagaa tcccactgct gcgaaacttt   300
cacactttcc tctatgagcc ggagtggcgg ttcaccgaga gcaaggagaa gcaccgagta   360
gtgctggagg acttccccac gatctccctg gagtttagaa atttggctga aaatatcaa    420 acagtgatcg ctgacatctg tcacaggatg ggatgtggga tggcagaatt tctaaacaag   480
gatgtaacct ccaaacagga ctgggacaag tactgtcact atgttgctgg actggtggga   540
atcggccttt ctcgcctatt ctctgcctca gagtttgaag atcccatagt tggtgaagac   600
acagagtgtg ccaattctat gggtctgttt ctgcagaaaa caaatatcat tcgtgattat   660
ctggaagacc aacaagaagg aagacagttt tggcctcaag aggtatgggg caaatatgtt   720
aagaagctgg aagactttgt taagccagag aacgtagatg tggccgtgaa gtgcttgaat   780
gaactcataa ccaacgccct acaacacatc cctgacgtca tcacctacct gtcaaggctc   840
cggaaccaaa gtgtgtttaa cttctgtgcc attccacagg taatggccat tgctacgctg   900
gctgcctgtt acaataacca tcaggtattc aaggagtag tgaagattcg aaggggcaa    960 gcagttaccc tcatgatgga tgccaccaac atgccagctg tcaaagctat catataccag  1020
```

```
tacatagaag agatttatca ccgggtcccc aactcagacc cgtcagctag caaggccaag      1080
cagctcatct ccaacatcag gacgcagagc tga                                  1113
```

<210> SEQ ID NO 22
<211> LENGTH: 1398
<212> TYPE: DNA
<213> ORGANISM: Botryococcus braunii

<400> SEQUENCE: 22

```
atggtgaaac tcgtcgaggt tttgcagcac ccggacgaga tcgtccccat cctgcagatg       60
ttgcataaga cctaccgcgc aaagcgcagc tataaagacc tggtctggc cttttgctac      120 ggaatgttgc aacgggtttc gagaagcttt tcagtagtta tacagcagct gcctgacgaa      180
ttgcgccatc caatatgcgt gttttatctt attcttcggg ccctggatac tgtcgaggat      240
gacatgaacc tcccaaatga agttaaaata cctcttcttc gccacttcca tgaacatctc      300
tttgacaggt cgtggaagct caaatgtgga tatggaccgt atgtagattt gatggagaac      360
tatccgctgg tcacggatgt cttccttaca ctctctccag gcgcacagga ggtaatccgg      420
gacagcacgc gccgcatggg caatggcatg gccgacttca ttggcaagga tgaggtccac      480
tcagtagcgg agtatgatct gtactgtcac tatgtggctg gcttggtcgg gagtgctgtg      540
gccaagattt tgtggacag cgggctggag aaggagaatc tggtcgcaga ggtggatctg      600
gccaacaaca tgggccagtt cctgcaaaag accaacgtta ttcgagacta cttggaggat      660
attaatgaag aaccggcccc taggatgttc tggccgcggg agatctgggg caaatatgcc      720
caggagctgg cggacttcaa ggacccagcc aatgagaaag cggcggtaca gtgcctgaat      780
cacatggtca cagatgcact ccgacactgc gagatcggcc tgaacgtgat cccgctgttg      840
cagaacattg gcatcctccg cagctgcctc atccccgaag tcatgggctt gagaaccctg      900
accttgtgtt acaacaatcc tcaagtcttc cgaggggtgg tgaagatgcg gagaggggag      960
actgccaagc tgttcatgag tatctacgac aagcgctcct tctaccaaac atatctccga     1020
ctcgcgaacg agttggaagc aaaatgtaaa ggggaggcga gtggagaccc catggtggcc     1080
acaacgctga gcatgtgca cggaatccag aagtcatgca aagccgctct cagcagcaaa     1140
gagctgcttg ccaagtctgg ctcggcccct cacagacgatc ccgctatcag gttgctgctg     1200
ctggtgggag tcgtggccta ctttgcatac gcattcaact tggagatgt gcggggagag     1260 cacggggtgc gggctctggg ctccattctg gacctgtccc agaaaggctt ggctgtggcg     1320
agtgtcgctc tgctgctgct ggtgcttctg ccaggagcc gccttcctt gctcacctct     1380 gcttcttcca agcagtag                                                 1398
```

<210> SEQ ID NO 23
<211> LENGTH: 465
<212> TYPE: PRT
<213> ORGANISM: Botryococcus braunii

<400> SEQUENCE: 23

```
Met Val Lys Leu Val Glu Val Leu Gln His Pro Asp Glu Ile Val Pro
1               5                  10                  15

Ile Leu Gln Met Leu His Lys Thr Tyr Arg Ala Lys Arg Ser Tyr Lys
            20                  25                  30

Asp Pro Gly Leu Ala Phe Cys Tyr Gly Met Leu Gln Arg Val Ser Arg
        35                  40                  45

Ser Phe Ser Val Val Ile Gln Gln Leu Pro Asp Glu Leu Arg His Pro
    50                  55                  60
```

```
Ile Cys Val Phe Tyr Leu Ile Leu Arg Ala Leu Asp Thr Val Glu Asp
65                  70                  75                  80

Asp Met Asn Leu Pro Asn Glu Val Lys Ile Pro Leu Leu Arg Thr Phe
                85                  90                  95

His Glu His Leu Phe Asp Arg Ser Trp Lys Leu Lys Cys Gly Tyr Gly
            100                 105                 110

Pro Tyr Val Asp Leu Met Glu Asn Tyr Pro Leu Val Thr Asp Val Phe
        115                 120                 125

Leu Thr Leu Ser Pro Gly Ala Gln Glu Val Ile Arg Asp Ser Thr Arg
    130                 135                 140

Arg Met Gly Asn Gly Met Ala Asp Phe Ile Gly Lys Asp Glu Val His
145                 150                 155                 160

Ser Val Ala Glu Tyr Asp Leu Tyr Cys His Tyr Val Ala Gly Leu Val
                165                 170                 175

Gly Ser Ala Val Ala Lys Ile Phe Val Asp Ser Gly Leu Glu Lys Glu
            180                 185                 190

Asn Leu Val Ala Glu Val Asp Leu Ala Asn Asn Met Gly Gln Phe Leu
        195                 200                 205

Gln Lys Thr Asn Val Ile Arg Asp Tyr Leu Glu Asp Ile Asn Glu Glu
    210                 215                 220

Pro Ala Pro Arg Met Phe Trp Pro Arg Glu Ile Trp Gly Lys Tyr Ala
225                 230                 235                 240

Gln Glu Leu Ala Asp Phe Lys Asp Pro Ala Asn Glu Lys Ala Ala Val
                245                 250                 255

Gln Cys Leu Asn His Met Val Thr Asp Ala Leu Arg His Cys Glu Ile
            260                 265                 270

Gly Leu Asn Val Ile Pro Leu Leu Gln Asn Ile Gly Ile Leu Arg Ser
        275                 280                 285

Cys Leu Ile Pro Glu Val Met Gly Leu Arg Thr Leu Thr Leu Cys Tyr
    290                 295                 300

Asn Asn Pro Gln Val Phe Arg Gly Val Val Lys Met Arg Arg Gly Glu
305                 310                 315                 320

Thr Ala Lys Leu Phe Met Ser Ile Tyr Asp Lys Arg Ser Phe Tyr Gln
                325                 330                 335

Thr Tyr Leu Arg Leu Ala Asn Glu Leu Glu Ala Lys Cys Lys Gly Glu
            340                 345                 350

Ala Ser Gly Asp Pro Met Val Ala Thr Thr Leu Lys His Val His Gly
        355                 360                 365

Ile Gln Lys Ser Cys Lys Ala Ala Leu Ser Ser Lys Glu Leu Leu Ala
    370                 375                 380

Lys Ser Gly Ser Ala Leu Thr Asp Asp Pro Ala Ile Arg Leu Leu Leu
385                 390                 395                 400

Leu Val Gly Val Val Ala Tyr Phe Ala Tyr Ala Phe Asn Leu Gly Asp
                405                 410                 415

Val Arg Gly Glu His Gly Val Arg Ala Leu Gly Ser Ile Leu Asp Leu
            420                 425                 430

Ser Gln Lys Gly Leu Ala Val Ala Ser Val Ala Leu Leu Leu Leu Val
        435                 440                 445

Leu Leu Ala Arg Ser Arg Leu Pro Leu Leu Thr Ser Ala Ser Ser Lys
    450                 455                 460

Gln
465
```

<210> SEQ ID NO 24
<211> LENGTH: 1212
<212> TYPE: DNA
<213> ORGANISM: Botryococcus braunii

<400> SEQUENCE: 24

```
atgactatgc accaagacca cggagtcatg aaagaccttg tcaagcatcc aaatgaattt    60
ccatacttgc tccaactagc tgcaacaacg tacggctcac cggctgcacc gatcccaag    120
gaaccggacc gagcttctg ctacaatact cttcacaccg tttcgaaggg gttccccaga   180
tttgttatga gacttccgca ggaactccaa gatccgatat gcatattcta cctcctgttg   240
cgagcactag acacggtgga ggatgatatg aacctcaaaa gtgagacgaa gatttcactc   300
ctacgcgttt tccatgaaca ctgttcagac aggaactgga gtatgaaaag tgattatggc   360
atatatgcag atctgatgga aagattcccc ctggtcgtat ccgtcttaga gaagctccct   420
cccgccacac agcagacttt cagggagaat gtcaaataca tgggcaatgg catggcagat   480
tttattgata agcagatcct gacagtggat gagtacgacc tctactgcca ctatgtggcc   540
ggcagttgcg gcattgctgt caccaaggtc attgtgcagt tcaaccttgc cacgcctgaa   600
gctgactcct acgacttttc caacagtctg ggcctcttgc ttcagaaggc caacatcatc   660
actgactaca atgaagacat caatgaagag cccaggccca ggatgttctg ccccaggag   720
atttggggga agtacgcgga gaagttggct gacttcaatg aacccgaaaa tattgataca   780
gccgtgaagt gcttgaacca catggtcaca gatgcaatgc ggcacattga ccttccctc    840
aaaggcatgt tttatttcac agacaagaca gtctttcggg cgctcgctct tctgctggtc   900
acagcctttg ccatttgtc cactttgtac aacaacccca atgtctttaa agagaaagtg   960
agacagcgga agggaaggat tgcacggctg gtcatgtcat ccaggaatgt accaggcctc  1020
ttccgtacat gcctcaaact cgcaaacaac ttcgagtcca ggtgcaagca agagacggca  1080
aatgatccca ctgtggccat gactatcaag cgcttgcaat ctattcaagc tacatgcaga  1140
gatggcctgg ccaagtatga cacaccctct gggctgaaat ctttctgcgc agccccaact  1200
cccaccaagt ga                                                      1212
```

<210> SEQ ID NO 25
<211> LENGTH: 403
<212> TYPE: PRT
<213> ORGANISM: Botryococcus braunii

<400> SEQUENCE: 25

Met Thr Met His Gln Asp His Gly Val Met Lys Asp Leu Val Lys His
1               5                   10                  15

Pro Asn Glu Phe Pro Tyr Leu Leu Gln Leu Ala Ala Thr Thr Tyr Gly
            20                  25                  30

Ser Pro Ala Ala Pro Ile Pro Lys Glu Pro Asp Arg Ala Phe Cys Tyr
        35                  40                  45

Asn Thr Leu His Thr Val Ser Lys Gly Phe Pro Arg Phe Val Met Arg
    50                  55                  60

Leu Pro Gln Glu Leu Gln Asp Pro Ile Cys Ile Phe Tyr Leu Leu Leu
65                  70                  75                  80

Arg Ala Leu Asp Thr Val Glu Asp Asp Met Asn Leu Lys Ser Glu Thr
                85                  90                  95

Lys Ile Ser Leu Leu Arg Val Phe His Glu His Cys Ser Asp Arg Asn
            100                 105                 110

```
Trp Ser Met Lys Ser Asp Tyr Gly Ile Tyr Ala Asp Leu Met Glu Arg
            115                 120                 125

Phe Pro Leu Val Val Ser Val Leu Glu Lys Leu Pro Pro Ala Thr Gln
        130                 135                 140

Gln Thr Phe Arg Glu Asn Val Lys Tyr Met Gly Asn Gly Met Ala Asp
145                 150                 155                 160

Phe Ile Asp Lys Gln Ile Leu Thr Val Asp Glu Tyr Asp Leu Tyr Cys
                165                 170                 175

His Tyr Val Ala Gly Ser Cys Gly Ile Ala Val Thr Lys Val Ile Val
            180                 185                 190

Gln Phe Asn Leu Ala Thr Pro Glu Ala Asp Ser Tyr Asp Phe Ser Asn
        195                 200                 205

Ser Leu Gly Leu Leu Leu Gln Lys Ala Asn Ile Ile Thr Asp Tyr Asn
210                 215                 220

Glu Asp Ile Asn Glu Glu Pro Arg Pro Arg Met Phe Trp Pro Gln Glu
225                 230                 235                 240

Ile Trp Gly Lys Tyr Ala Glu Lys Leu Ala Asp Phe Asn Glu Pro Glu
                245                 250                 255

Asn Ile Asp Thr Ala Val Lys Cys Leu Asn His Met Val Thr Asp Ala
            260                 265                 270

Met Arg His Ile Glu Pro Ser Leu Lys Gly Met Val Tyr Phe Thr Asp
        275                 280                 285

Lys Thr Val Phe Arg Ala Leu Ala Leu Leu Leu Val Thr Ala Phe Gly
290                 295                 300

His Leu Ser Thr Leu Tyr Asn Asn Pro Asn Val Phe Lys Glu Lys Val
305                 310                 315                 320

Arg Gln Arg Lys Gly Arg Ile Ala Arg Leu Val Met Ser Ser Arg Asn
                325                 330                 335

Val Pro Gly Leu Phe Arg Thr Cys Leu Lys Leu Ala Asn Asn Phe Glu
            340                 345                 350

Ser Arg Cys Lys Gln Glu Thr Ala Asn Asp Pro Thr Val Ala Met Thr
        355                 360                 365

Ile Lys Arg Leu Gln Ser Ile Gln Ala Thr Cys Arg Asp Gly Leu Ala
370                 375                 380

Lys Tyr Asp Thr Pro Ser Gly Leu Lys Ser Phe Cys Ala Ala Pro Thr
385                 390                 395                 400

Pro Thr Lys

<210> SEQ ID NO 26
<211> LENGTH: 1152
<212> TYPE: DNA
<213> ORGANISM: Artificial Sequence
<220> FEATURE:
<223> OTHER INFORMATION: Synthetic polynucleotide

<400> SEQUENCE: 26
atgaaacttc gggaagtctt gcagcacccg ggtgagatta tccctctcct gcaaatgatg      60
gtcatggcct accgcaggaa gaggaagcct caagatccca atttggcctg gtgctgggag     120
acgctgatta agtttcgag aagttacgtt ctagtcattc agcagcttcc tgaagtactt     180
caggacccta tctgcgtcaa ctatcttgtt cttcgaggct ggacacact gcaggatgac     240 atggcaattc ccgcagagaa gcgggttcca ctcctcctcg actactacaa ccatattgga     300
gacataactt ggaagccgcc ttgcggatat gggcagtatg tggagctgat tgaggagtat     360
ccaagggtga caaaagagtt cttgaaactc aacaagcaag atcagcagtt tatcacggac     420
```

-continued

```
atgtgcatgc ggctgggagc ggagatgaca gtatttctca agagggacgt gttgacagtt    480
cctgacttgg atctgtatgc cttcactaat aacgggccag ttgctatctg cctgaccaag    540
ttatgggtgg acagaaagtt tgcagaccca agcttctgg accgggagga cctatcgggc     600
cacatggcca tgttcttggg caagattaac gtcatccgcg acatcaagga ggatgtcttg    660
gaggatcctc ctcgcatctg gtggccgaag gagatctggg gaaagtacct caaggacctg    720
agggacatca tcaagcctga gtatcaaaag gaagcgctgg cctgtctcaa tgacatcctc    780
acagatgcac tgcgccatat cgagccctgc cttcagtaca tggagatggt ttgggacgag    840
ggcgttttta gttctgcgc cgtgccagag ctcatgtcct ggctaccat ctcggtgtgt      900
tacaacaatc cgaaggtctt cacaggtgtt gtcaagatga ggaggggcga aacagcaaag    960
ctgtttctga gcgtaacaaa tatgccagct ctgtacaaga gtttttcagc cattgctgaa    1020
gaaatggagg ccaagtgtgt gagggaggat cccaactttg cactcacagt caagcggctt    1080
caggatgtcc aggcgttatg caaggcaggc ctagcaaaat caaatggaaa ggtttcagct    1140
aagggtgctt ag                                                         1152

<210> SEQ ID NO 27
<211> LENGTH: 383
<212> TYPE: PRT
<213> ORGANISM: Botryococcus braunii

<400> SEQUENCE: 27

Met Lys Leu Arg Glu Val Leu Gln His Pro Gly Glu Ile Ile Pro Leu
1               5                   10                  15

Leu Gln Met Met Val Met Ala Tyr Arg Arg Lys Arg Lys Pro Gln Asp
                20                  25                  30

Pro Asn Leu Ala Trp Cys Trp Glu Thr Leu Ile Lys Val Ser Arg Ser
            35                  40                  45

Tyr Val Leu Val Ile Gln Gln Leu Pro Glu Val Leu Gln Asp Pro Ile
        50                  55                  60

Cys Val Asn Tyr Leu Val Leu Arg Gly Leu Asp Thr Leu Gln Asp Asp
65                  70                  75                  80

Met Ala Ile Pro Ala Glu Lys Arg Val Pro Leu Leu Asp Tyr Tyr
                85                  90                  95

Asn His Ile Gly Asp Ile Thr Trp Lys Pro Pro Cys Gly Tyr Gly Gln
            100                 105                 110

Tyr Val Glu Leu Ile Glu Glu Tyr Pro Arg Val Thr Lys Glu Phe Leu
        115                 120                 125

Lys Leu Asn Lys Gln Asp Gln Gln Phe Ile Thr Asp Met Cys Met Arg
    130                 135                 140

Leu Gly Ala Glu Met Thr Val Phe Leu Lys Arg Asp Val Leu Thr Val
145                 150                 155                 160

Pro Asp Leu Asp Leu Tyr Ala Phe Thr Asn Asn Gly Pro Val Ala Ile
                165                 170                 175

Cys Leu Thr Lys Leu Trp Val Asp Arg Lys Phe Ala Asp Pro Lys Leu
            180                 185                 190

Leu Asp Arg Glu Asp Leu Ser Gly His Met Ala Met Phe Leu Gly Lys
        195                 200                 205

Ile Asn Val Ile Arg Asp Ile Lys Glu Asp Val Leu Glu Asp Pro Pro
    210                 215                 220

Arg Ile Trp Trp Pro Lys Glu Ile Trp Gly Lys Tyr Leu Lys Asp Leu
225                 230                 235                 240
```

```
Arg Asp Ile Ile Lys Pro Glu Tyr Gln Lys Glu Ala Leu Ala Cys Leu
            245                 250                 255

Asn Asp Ile Leu Thr Asp Ala Leu Arg His Ile Glu Pro Cys Leu Gln
            260                 265                 270

Tyr Met Glu Met Val Trp Asp Glu Gly Val Phe Lys Phe Cys Ala Val
        275                 280                 285

Pro Glu Leu Met Ser Leu Ala Thr Ile Ser Val Cys Tyr Asn Asn Pro
        290                 295                 300

Lys Val Phe Thr Gly Val Val Lys Met Arg Arg Gly Glu Thr Ala Lys
305                 310                 315                 320

Leu Phe Leu Ser Val Thr Asn Met Pro Ala Leu Tyr Lys Ser Phe Ser
            325                 330                 335

Ala Ile Ala Glu Glu Met Glu Ala Lys Cys Val Arg Glu Asp Pro Asn
            340                 345                 350

Phe Ala Leu Thr Val Lys Arg Leu Gln Asp Val Gln Ala Leu Cys Lys
            355                 360                 365

Ala Gly Leu Ala Lys Ser Asn Gly Lys Val Ser Ala Lys Gly Ala
    370                 375                 380
```